United States Patent [19]
Potempa et al.

[11] Patent Number: 5,593,897
[45] Date of Patent: Jan. 14, 1997

[54] BINDING OF IMMUNE COMPLEXES BY MODIFIED FORMS OF C-REACTIVE PROTEIN

[75] Inventors: Lawrence A. Potempa, Deerfield; Byron E. Anderson, Morton Grove, both of Ill.

[73] Assignee: Northwestern University, Evanson, Ill.

[21] Appl. No.: 271,137

[22] Filed: Jul. 6, 1994

Related U.S. Application Data

[63] Continuation of Ser. No. 582,884, filed as PCT/US89/01247, Mar. 31, 1989, abandoned, which is a continuation-in-part of Ser. No. 176,923, Apr. 4, 1988, abandoned.

[51] Int. Cl.⁶ ............ G01N 33/564; G01N 33/543; G01N 33/53; A61M 1/38
[52] U.S. Cl. .......... 436/507; 436/518; 436/524; 436/528; 436/532; 436/538; 436/541; 436/544; 436/824; 435/7.9; 435/7.92; 422/61; 604/6
[58] Field of Search .................. 435/7.9, 7.92, 435/2; 422/61, 285; 436/507, 518, 538, 541, 544, 824, 524, 528, 532; 530/413, 810; 604/6

[56] References Cited

U.S. PATENT DOCUMENTS

| | | | |
|---|---|---|---|
| 3,882,225 | 5/1975 | Patel et al. | 436/579 |
| 4,230,685 | 10/1980 | Senyei et al. | 436/526 |
| 4,409,330 | 10/1983 | Pollard, Jr. | 435/178 |
| 4,418,152 | 11/1983 | Hosaka et al. | 436/511 |
| 4,432,871 | 2/1984 | Yamawski et al. | 210/195.1 |
| 4,447,545 | 5/1984 | De Fazio et al. | 436/518 |
| 4,450,239 | 5/1984 | Chatterton | 436/527 |
| 4,464,165 | 8/1984 | Pollard, Jr. | 604/5 |
| 4,470,967 | 9/1984 | Gough et al. | 424/89 |
| 4,504,585 | 3/1985 | Reynolds | 436/518 |
| 4,551,435 | 11/1985 | Liberti et al. | 436/541 |
| 4,608,253 | 8/1986 | Obnishi et al. | 424/194.3 |
| 4,614,513 | 9/1986 | Bensinger | 604/6 |
| 4,617,262 | 10/1986 | Maxim et al. | 435/28 |
| 4,627,915 | 12/1986 | Kuroda et al. | 210/195.2 |
| 4,634,417 | 1/1987 | Korec | 604/4 |
| 4,656,144 | 4/1987 | Hosaka et al. | 436/534 |
| 4,775,483 | 10/1988 | Mookerjea et al. | 210/670 |
| 4,801,449 | 1/1989 | Balint et al. | 424/85.8 |
| 4,875,314 | 8/1989 | O'Connor et al. | 424/85.1 |
| 4,889,816 | 12/1989 | Davis et al. | 436/518 |
| 4,902,630 | 2/1990 | Bennett et al. | 436/546 |
| 5,037,649 | 8/1991 | Balint et al. | 424/85.8 |
| 5,084,398 | 1/1992 | Huston et al. | 436/535 |
| 5,272,258 | 12/1993 | Siegel et al. | 530/388.25 |
| 5,283,238 | 2/1994 | Potempa et al. | 514/12 |

FOREIGN PATENT DOCUMENTS

WO89/04675  6/1989  WIPO .............. A61M 1/36

OTHER PUBLICATIONS

Ballou et al., *J. Lab. Clin. Med.*, 115, 332–338 (1990).
Gotschlich, *Ann. N.Y. Acad. Sci.*, 557, 9–18 (1989) Review on CRP.
Harris et al., *FASEB J.*, 4, A 1995 (1990) Abstract No. 1759.
Horowitz et al., *J. Immunol.*, 138, 2598–2603 (1987).
James et al., *Rheumatology News*, 18, 3 (1990).
Mortensen et al., *J. Immunol.*, 119, 1611–1616 (1977).
Swanson et al., *FASEB J.*, 4, A 1840 (1990) Abstract No. 856.
Bray et al., *J. Immunol.*, 140, 4271–4278 (1988).
Chu et al., *Proc. Amer. Acad. Cancer Res.*, 28, 344 (1987) Abstract No. 1362.
Chu et al., *Proc. Amer. Acad. Cancer Res.*, 30, (1989) Abstract p. 48.
Bristow et al., *Molec. Immunol.*, 23, 1045–1052 (1986).
deBeer et al., *J. Exp. Med.*, 154, 1134–1149 (1981).
Fiedel et al., *J. Immunol.*, 131, 1416–1419 (1983).
Floyd-Smith et al., *Immunogenetics*, 24, 171–176 (1986).
Gewurz et al., *FASEB J.*, 4, A 2198 (1990) Abstract No. 2911.
Ku et al., *FASEB J.*, 4, A 1770 (1990) Abstract No. 449.
Mantzouranis et al., *J. Biol. Chem.*, 260, 7752–56 (1985).
Pepys et al., *Clin. Exp. Immunol.*, 38, 284–93 (1979).
Prelli et al., *J. Biol. Chem.*, 260, 12895–98 (1985).
Burton et al., *Nature*, 288, 338–344 (1980).
Duncan et al., *Nature*, 332, 738–740 (1988).
Hughes-Jones et al., *Immunol.*, 34, 459–463 (1978).
Lancet et al., *Biochem. Biophys. Res. Commun.*, 85, 608–614 (1978).
Langone, *Adv. Immunol.*, 32, 157–252 (1982).
Langone et al., *J. Immunol.*, 121, 327–332 (1978).
Lukas et al., *J. Immunol.*, 127, 2555–2560 (1981).
Veerhuis et al., *Eur. J. Immunol.*, 15, 881–887 (1985).
Jones et al., *Plasma Ther. Transfus. Technol.*, 7, 333–349 (1986).

(List continued on next page.)

*Primary Examiner*—Kay K. A. Kim
*Attorney, Agent, or Firm*—Brinks Hofer Gilson & Lione

[57] ABSTRACT

A method of binding aggregated immunoglobulin or immune complexes comprising contacting them with modified forms of C-reactive protein. The method may be employed for diagnostic and therapeutic purposes and to deplete fluids of aggregated immunoglobulin or immune complexes. Further, a method of reducing the levels of immune complexes in a mammal comprising administering modified-CRP to the mammal, and a method of binding immunoglobulins comprising contacting them with modified C-reactive protein. Also, a method of binding aggregated immunoglobulin or immune complexes comprising contacting them with antibody to neo-CRP, and a method of modifying C-reactive protein. Finally, a test kit for detecting or quantitating immune complexes and a device for removing aggregated immunoglobulin or immune complexes from fluids are disclosed.

19 Claims, 5 Drawing Sheets

OTHER PUBLICATIONS

Jones et al., *J. Immunological Methods*, 53, 201–208 (1982).
Levinson et al., *J. Clin. Immunoassay*, 7, 328 (1984).
Harris et al, *FASEB J.*, 4, A 1893 (1990) Abstract No. 1163.
Iturralde et al., *Revista Española de Fisiologia*, 40, 279–288 (1984).
Kinoshita et al., *Biochem.*, 28, 9840–48 (1989).
Rees et al., *Clin. Res.*, 37, 559A (1989) Abstract.
Ying et al., *FASEB J.*, 3, A 1345 (1989) Abstract No. 6504.
Ying et al., *J. Immunol.*, 143, 221–228 (1989).
Baltz et al. (1982) *Biochim Biophys Acta* 701:229–236.
Anderson et al., *Immunol. Today*, 7, 264–66 (1986).
Baltz et al., *Ann N.Y. Acad. Sci.*, 389, 49–75 (1982).
Barna et al., *Cancer Res.*, 44, 305–310 (1984).
Barna et al., *Cancer Res.*, 47, 3959–63 (1987).
Bertram et al., *J. Biol. Resp. Mod.*, 3, 235–240 (1984).
Blair et al., *J. Immunol. Methods*, 59, 129–143 (1983).
Boackle et al., *Nature*, 282, 742–43 (1979).
Bombardieri et al., *J. Art. Org.*, 6, 47–50 (1983).
Bray et al., *Clin Immunol. Newsletter*, 8, 137–140 (1987).
Bray et al., *Clin. Res.*, 35, 889A (1987).
Bruneau et al., *J. Clin. Invest.*, 64, 191–198 (1979).
Burton, *Molec. Immunol.*, 22, 161–206 (1985).
Chu et al., *Proc. Amer. Assoc. Cancer Res.*, 29, 371 (1988) Abstract No. 1477.
Chudwin et al., *J. Allergy Clin. Immunol.*, 77, 216a (1986).
Colbert et al., *J. Biol. Resp. Mod.*, 3, 255–59 (1984).
Creighton et al., *J. Immunol.*, 111, 1219–1227 (1973).
Deodhar et al., *Cancer Res.*, 42, 5084–88 (1982).
Dobre et al., *J. Immunol. Meth.*, 66, 171–178 (1984).
Dougherty et al., *Protides of the Biological Fluids*, 34, 291–293 (1986).
Emancipator et al., *Lab. Invest.*, 54, 475–478 (1986).
Feldmann et al., *J. Exp. Med.*, 131, 247–274 (1970).
Feldkamp, *Clin. Chem. News*, 4, 5–6 (1987).
Friquet et al., *Molec. Immunol.*, 21, 673–77 (1984).
Gauthier et al., *J. Exp. Med.*, 156, 766–777 (1982).
Gewurz et al., *Advances in Internal Medicine*, 27, 345–72 (1982).
Gotschlich et al., *Proc. Nat'l Acad. Sci.*, 57, 706–712 (1967).
Gupta et al., *Arthritis and Rheumatism*, 31, R39a, (1988) Abstract No. 325.
Gupta et al., *Journal of Immunology*, 137, 2173–2179 (1986).
Hay et al., *Clin. Exp. Immunol.*, 24, 396–400 (1976).
Ingram, *Animal Models of Immunological Processes*, 221–253 (1982) J. Hay ed, Academic Press, London.
James, *Dissertation Abstracts International*, 41/08–B, 2963 (1980).
Jones et al., *Cancer*, 46, 675–84 (1980).
Kaplan et al., *J. Immunol.*, 112, 2135–2147 (1974).
Kearney et al., *Immunological Communications*, 11, 275–282 (1982).
Kilpatrick and Volanakis, *J. Immunol.*, 134, 3364–70 (1985).
Kinoshita, *F.A.S.E.B. J.*, 2, A1149 (1988) Abstract No. 4959.
Kulkarni et al., *Cancer Res.*, 41, 2700–2706 (1981).
Lai et al., *Artifical Organs*, 11, 259–264 (1987).
Lei et al., *J. Biol. Chem.*, 260, 13377–83 (1985).
Levinsky et al., *Lancet*, i, 564–67 (1977).
Levinson et al., *J. Clin. Immunoassay*, 7, 328–336 (1984).
Liberti et al., *J. Immunol.*, 123, 2212–2219 (1979).
Liberti, *Opportunities in the Oncology Marketplace* (Slide presentation). Date ?.
Maire et al., *Clin. Exp. Immunol.*, 51, 215–224 (1983).
Malchesky et al., *Cleveland Clinic Quarterly*, 50, 11–18 (1983).
Mantzouranis et al., *Ped. Res.*, 18, 260A (1984) Abstract No. 987.
Maudsley and Pepys, *Immunology*, 62, 17–22 (1987).
McDougal et al., *Adv. Clin. Chem.*, 24, 1–60 (1985).
Mingari et al., *J. Immunol.*, 121, 767–770 (1978).
Mold et al., *J. Exp. Med.*, 154, 1703–1708 (1981).
Mortensen, et al., *J. Immunol.*, 117, 774–781 (1976).
Nakayama et al., *J. Immunol.*, 128, 2435–2438 (1982).
Nakayama et al., *J. Immunol.*, 132, 1336–1340 (1984).
Nauts, *Host Defense Against Cancer and Its Potentiation*, 337–351 (1975).
Mizuno et al Eds, Univ Tokyo Press, Tokyo.
Nguyen et al., *J. Biol. Chem.*, 261, 10450–10455 (1986).
Nilsson et al., *Plasma. Ther. Transfers. Technol.*, 5, 127–134 (1984).
Nilsson et al., *Scand. J. Haematol.*, 30, 458–464 (1983).
Nilsson et al., *Factor VIII Inhibitors*, 225 (1984).
Nilsson, *Int. Arch. Allergy*, 32, 545–62 (1967).
Osmand et al., *Proc. Nat'l Acad. Sci.*, 74, 1214–1218 (1977).
Pereira et al., *J. Immunol.*, 125, 763–770 (1980).
Perussia et al., *J. Immunol.*, 133, 180–89 (1984).
Potempa et al., *Mol. Immunol.*, 24, 531–41 (1987).
Potempa et al., *J. Immunol.*, 127, 1509–1514 (1981).
Potempa et al., *Protides of the Biological Fluids*, 34, 287–290 (1986).
Potempa et al., *Inflammation*, 12, 391–405 (1988).
Potempa et al., *Mol. Immunol.*, 20, 1165–1175 (1983).
Randerson et al., *Artificial Organs*, 6, 43–49 (1982).
Rawer et al., *J. Art. Org.*, 6, 97–101 (1983).
Ritzmann et al., *Clin. Chem.*, 28, 1259–71 (1982).
Rizk et al., *Cancer*, 58, 55–61 (1986).
Robey et al., *J. Biol. Chem.*, 262, 7053–57 (1987).
Samberg et al., *Cell. Immunol.*, 116, 86–98 (1988).
Samols et al., *Biochem. J.*, 227, 759–65 (1985).
Schena et al., *J. Art. Org.*, 6, 29–33 (1983).
Schur, *N. Eng. J. Med.*, 298, 161–162, (1978).
Singh et al., *J. Immunol. Meth.*, 50, 109–114 (1982).
Sjodahl, *Eur. J. Biochem.*, 78, 471–90 (1977).
Smith et al., *Cleveland Clinic Quarterly*, 51, 135–42, (1984).
Smith et al., *Plasmapheresis*, 51, 135–42 (1984).
Terman et al., *New Engl. J. Med.*, 305, 1195–2000 (1981).
Theofilopoulos et al., *J. Immunol.*, 119, 657–63 (1977).
Theofilopoulos et al., *J. Clin. Invest.*, 61, 1570–1581 (1978).
Theofilopoulos et al., *Hosp. Pract.*, 107–121 (1980).
Theofilopoulos et al., *Immunodiagnostics of Cancer*, 896–937 (1979).
Theofilopoulos et al., *Advances in Immunology*, 28, 89–220 (1979).
Thombre et al., *Cancer Immunol. Immunother.*, 16, 145–50 (1984).
Tillett and Francis, *J. Exp. Med.*, 52, 561–71 (1930).
Tseng et al., *Molec. Immunol.*, 25, 679–686 (1988).
Unkeless et al., *Adv. Immunol.*, 31, 247–70 (1981).
Volanakis et al., *J. Immunology*, 113, 9–17 (1974).
Volanakis and Kaplan, *Proc. Soc. Exp. Biol. Med.*, 136, 612–614 (1971).
Woo et al., *J. Biol. Chem.*, 260, 13384–88 (1985).
Zahedi et al., *Cancer Res.*, 46, 5077–83 (1986).
Zeller et al., *Fed. Proc.*, 46, 1033a (1987).
Zeller et al., *J. Lab. Clin. Med.*, 108, 567–76 (1986).
Zeller et al., *J. Leukocyte Biol.*, 40, 769–783 (1986).
Barnet et al., *Clin. Exp. Immunol.*, 51, 215–24 (1983).
Bray et al., *J. Leukocyte Biol.*, 42, 379 (1987) Abst. #152.

Fairbanks et al., *Fed. Proc.*, 42, 700 (1983) Abstr. #2390.
Gewurz et al., *Proc. Symp. Sur Les Monquers de l'Inflammation*, Lyon, France, 34 (1983).
Gewurz et al., *Proc. XXXIV Protides Biolg. Fluids*, No. 5 (1986).
Gewurz et al., *Hospital Practice*, 17, 67–81 (1982).
Hirai et al., *Protides of the Biol. Fluids*, 34, 283–86 (1986).
Kilpatrick et al., *Molec. Immunol.*, 19, 1159–65 (1982).
Landay et al., *Proc. XXXIVth Colloquium, Protides Biol. Fluids*, Abstract No. B3.23 (May 1986).
Maldonado et al., *Fed. Proc.*, 42, 961 (1983).
Nilsson et al., *Blood*, 58, 38–44 (1981).
Potempa et al., *Proc. Amer. Acad. Cancer Res.*, 28, 344 (1987).
Potempa et al., *J. Allergy Clin. Immunol.*, 77, 135 (1986) Abstr #60.
Potempa et al., *Fed. Proc.*, 41, 556 (1982) Abstr #1675.
Potempa et al., *Fed. Proc.*, 44, 1190 (1985).
Potempa et al., *F.A.S.E.B.*, 2, 731 (1988).
Rees et al., *Clin. Immunol. Immunopath.*, 48, 95–107 (1988).
Rees et al., *Fed. Proc.*, 45, 263 (1986).
Roux et al., *J. Immunol.*, 131, 2411–15 (1983).
Samberg et al., *Fed. Proc.*, 45, 262 (1986).
Samberg et al., *J. Leukocyte Biol.*, 42, 350 (1987) Abstr #65.
Schifferli et al., *New Eng. J. Med.*, 315, 488–95 (1986).
Siegel et al., *J. Exp. Med.*, 140, 631–47 (1974).
Tseng et al., *Hybridoma*, 7, 185–91 (1988).
Tsuruta et al., *Plasmapheresis*, 149–54 (1983).
Volanakis and Kearney, *J. Exp. Med.*, 153, 1604–14 (1981).
Young and Williams, *J. Immunol.*, 121, 1893–98 (1978).
Ying et al (1989) J. Immunol. 143:221–28.
Samols et al (1986) Prot. Biol. Fluids 34:263–66.
Ying et al (1992) Mol. Immunol. 29:677–687.
Kresl et al (1991) FASEB J. 5:633a.
Hu et al (1988) J. Biol. Chem. 263:1500–1504.
Nguyen et al (1986) J. Biol. Chem. 261:10456–10465.
Agrawal et al (1992) J. Biol. Chem. 267:25352–25358.

| GROUP | 5-FU | BUFFER | DAY 6 BODY WEIGHTS | MEAN LIFE SPAN |
|---|---|---|---|---|
| GROUP 1 | 0 | 0 | 16.8 g | 20 DAYS |
| GROUP 2 | 0 | LOW DOSE BUFFER | ≈ GROUP 1 | ≈ GROUP 1 |
| GROUP 3 | 0 | HIGH DOSE BUFFER | ≈ GROUP 1 | ≈ GROUP 1 |
| GROUP 4 | 20 mg/kg | 0 | 20% DECREASE FROM DAY 2 | ≈ GROUP 1 |

| GROUP | 5-FU | mCRP DOSE | DAY 6 BODY WEIGHTS | MEAN LIFE SPAN |
|---|---|---|---|---|
| GROUP 5 | 0 | 50 μg | ≈ DAY 2 | ≈ CONTROL |
| GROUP 6 | 0 | 200 μg | ≈ DAY 2 | ≈ CONTROL |
| GROUP 7 | 20 mg/kg | 50 μg | 10% DECREASE FROM DAY 2 | 40% DECREASE FROM CONTROL |
| GROUP 8 | 20 mg/kg | 200 μg | 10% DECREASE FROM DAY 2 | ≈ CONTROL |
| GROUP 9 | 10 mg/kg | 50 μg | ≈ CONTROL | 128% INCREASE FROM CONTROL |
| GROUP 10 | 10 mg/kg | 200 μg | ≈ CONTROL | 133% INCREASE FROM CONTROL |

BINDING OF IMMUNE COMPLEXES BY MODIFIED FORMS OF C-REACTIVE PROTEIN

This application is a continuation of application Ser. No. 07/582,884, filed Oct. 3, 1990 now abandoned, which is the national phase under 35 USC 371 of PCT/US 89/01247 filed on Mar. 31, 1989 which is a CIP of Ser. No. 07/176,923 filed on Apr. 4, 1988, now abandoned.

FIELD OF INVENTION

This invention relates to a method for binding immunoglobulin, aggregated immunoglobulin or immune complexes, including all immunoglobulin isotypes of mammals, particularly IgG, IgA, and IgM, using a modified form of C-reactive protein, a naturally-occuring protein. In particular, this invention relates to the use of modified C-reactive protein to bind immune complexes in the treatment of a variety of diseases and as part of assays for the detection and quantitation of immune complexes. The modified form of C-reactive protein may be used as a reagent that can bind immune complexes either when coated onto a solid surface or when added to a solution containing immune complexes. Preferred is modified C-reactive protein expressing the neo-CRP antigen.

The invention further relates to a method of preparing modified C-reactive protein, and to a method of binding aggregated immunoglobulin, immune complexes and immunoglobulin comprising contacting them with antibody to neo-CRP. Finally, the invention also relates to test kits for detecting and quantitating immune complexes and to devices for removing immune complexes and aggregated immunoglobulin from fluids.

BACKGROUND OF THE INVENTION

Immune complexes are formed by the binding of antibodies with antigens, sometimes in conjunction with other proteins. The antigens which form immune complexes include components of infectious organisms, other molecules foreign to the host organism, tumor-associated molecules and, in many diseases, normal tissue molecular components. Antibodies produced to an antigen are specific for the particular antigenic substance. Antibodies bind to antigens and essentially neutralize them by, e.g., altering the biologic activity of a toxin, neutralizing the infectivity of microorganisms, or by providing the recognition signal whereby the antibody plus bound antigen are removed from the circulation or tissues. When an antibody binds to an antigen, the antibody-antigen complex is termed an immune complex.

Antigen + Antibody = Antigen-Antibody Complexes foreign substance + immune system response = immune complexes Immune complexes are removed from the circulation and tissues by a variety of normal mechanisms such as by fixed macrophages found in the liver, spleen and lymph nodes, and by circulating macrophages. The formation of antibodies and immune complexes is part of the natural response of the individual to combat diseases, such as infections and cancer. The binding of antibodies to antigens and the removal of the immune complexes are the mechanisms by which antigens are neutralized, taken out of tissues and blood and degraded.

The continued presence of immune complexes in the circulation and their deposition in tissues, contributes to compromised immune system function and inflammatory pathology. Immune complexes can deposit in tissues such as the lung, kidney, heart and joints causing both transient and permanent damage to those organs. In cancer, it is thought that the immune complexes may block the proper function of immune mechanisms which would otherwise destroy the cancer cells and prevent the growth and spread of the cancer within the body.

There may be one or several reasons why circulating immune complexes are found in high levels in diseases. The antigens and the immune system responses may be near maximal, and the immune complexes formed may simply overwhelm the capacity of the systems for their removal. Alternatively, some mechanism may have compromised the efficiency of the immune complex removal system, or the nature of the antigens and antibodies involved may result in inefficient removal. Immune complexes are found to persist in many individuals with cancer, autoimmune, arthritic, and infectious diseases. Therefore, the binding and removal of immune complexes, by an extracorporeal device, may result in a clinical improvement of individuals with cancer and improve the effectiveness of other treatments for cancer, may result in the prevention of lesions in organs associated with immune complexes that occur in infectious diseases, and may prevent lesions in organ systems in arthritic and autoimmune diseases, as well as result in the clinical improvement of these latter diseases. Indeed, many published studies indicate that the removal of circulating immune complexes, or enhancing their clearance from the circulation, may constitute an effective therapeutic treatment. [See Theofilopoulos, A. M. and Dixon, F. J., *Adv. Immunol.*, 28:90–220 (1979); Theofilopolous, A. N. and Dixon, F. J., *Immunodiagnostics of Cancer*, p. 896 (M. Decker Inc., New York 1979)].

There can be a wide variety in the number of anti-body molecules which bind to antigen, and antigens are of various sizes and shapes, thus leading to wide variations in the sizes of the immune complexes. Some immune complexes can also affix complement proteins such as C1q and C3 which may result in larger, more heterogeneous structures. Some immune complexes stimulate leukocytes while others stimulate lymphocytes or platelets [See Ritzmann, et al., *Clin. Chem.*, 28:1259–71 (1982); Maire, et al., *Clin. Exp. Immunol.*, 51:215–224 (1983), and Schifferli, et al., *New Eng. J. Mad.*, 315:448–495 (1986)]. Immune complexes may remain in circulation for long periods of time and deposit in various tissues contributing to the inflammatory and erosive manifestations of autoimmune and other diseases [See Emancipator, et al., *Lab. Invest.*, 54:475–478 (1986)].

Circulating immune complexes may block or reduce the efficiency of the natural effector mechanisms of the immune system, as has been postulated for malignant transformations [See Feldman, et al., *J. Exp. Med.*, 131:247 (1970); Mingari, et al., *J. Immunol.*, 121:767 (1978); Theofilopoulos, et al., *J. Immunol.*, 119:657–663 (1977); Theofilopoulos, et al., *Immunodiagnostics of Cancer*, p. 896, M. Decker, New York (1979), and Levinsky, et al., *Lancet*, 1:564 (1977)]. The removal of immune complexes from the circulation may reduce many of the clinical problems associated with autoimmune and infectious diseases and cancer. For example, it is beneficial to monitor circulating immune complex levels in blood and to specifically bind and remove circulating immune complexes which may otherwise compromise immune system function or lead to acute or chronic inflammation. Accordingly, many investigators have approached the monitoring and removal of circulating immune complexes by devising assays and adsorbents to selectively react with circulating immune complexes while not reacting with uncomplexed immunoglobulins.

Methods used to assay for immune complexes include: physical separation using polyethylene glycol; reducing the temperature of the solution containing the immune complexes (i.e., cold precipitation); binding of the immune complexes to complement protein C1q or to antibodies specific to the complement protein C3 and C3 degradation products; binding of the immune complexes to rheumatoid factors; binding to the bovine protein conglutinin; or binding of the immune complexes to platelets or to the Raji lymphoblastoid cell line [See Theofilopoulos, et al., *Hosp. Pract.*, 107–121 (February 1980); Ingram, *Animal Models of Immunological Processes*, pp. 221–253 (1982); Levinson, et al., *J. Clin. Immunoassay*, 7:328–336 (1984); Singh, et al., *J. Immunol. Meth.*, 50:109–114 (1982); Hay, et al., *Clin. Ext. Immunol.*, 24:396–400 (1976); Pereira, et al., *J. Immunol.*, 125:763–770 (1980); Theofilopoulos, et al., *J. Clin. Invest.*, 61:1570 (1978); Creighton, et al., *J. Immunol.*, 111:1219 (1973); Schur, *N. Engl. J. Med.*, 298:161 (1978), and Bruneau, et al., *J. Clin. Invest.*, 64:191 (1979)]. There are advantages to each assay, as well as disadvantages which include insensitivity, nonspecificity, inability to detect immune complexes of all sizes and of all immunoglobulin isotypes and subisotypes, reliance on immune complexes containing complement proteins, and interference by non-complexed immunoglobulins. It also appears that the ability to detect circulating immune complexes in serum from a patient with a specific disease varies with the assay used. [See McDougal, J. S., et al., *Adv. Clin. Chem.*, 24:1–60 (1985)]. Therefore, results gathered by any of the aforementioned assays may be considered to be of marginal value for diagnostic purposes, but may be used to support a diagnosis, to assess disease severity by correlating with amounts of immune complexes, or to monitor follow-up after therapeutic treatment as suggested by Feldkamp in *Clin. Chem. News*, 3:5–6 (1987).

Methods of removing circulating immune complexes from blood have emphasized a plasma exchange or blood filtration therapy. Generally, for blood filtration therapy, a substance which can bind complexed immunoglobulin is immobilized on a solid support which is encased online, through which the blood or plasma removed from the patient is passed. In some cases, after passage over the adsorbent (in an extracorporeal device), blood components are reinfused into the patient thus eliminating the need for large amount of replacement plasma or other replacement fluids.

Currently, there is interest in study of the use of Staphlococcal Protein A (the various subtypes being collectively known as "Protein A") as the immobilized circulating immune complex adsorbent. Some trials by investigators have resulted in promising results while others have failed, presumably due to Protein A's inability to effectively differentiate immunoglobulin in immune complexes from non-complexed immunoglobulin and to whatever effect this bacterial product has on stimulating pyrogenic activity, complement activation and general immune system reactivity as reported by Betram, et al., *J. Biol. Resp. Mod.*, 3:235–240 (1984); Terman, et al., *New Engl. J. Med.*, 305:1195–2000 (1981); Dobre, et al., *J. Immunol. Meth*, 66:171–178 (1984); Nilsson, et al., *Scand. J. Haematol.*, 30:458–464 (1983), and Nauts, in *Host Defense Against Cancer and Its Potentiation*, pp. 337–351 (1975).

Protein A binds to the "Fc" portion of immunoglobulins. Other investigators have proposed or attempted using other Fc receptors, such as C1q or rheumatoid factor, or a specific antigen or antibody, as immobilized immunoadsorbents. [See Nilsson, I. M., et al., *Plasma. Ther. Transfers. Technol.*, 5:127–134 (1984); Lai, K. N., et al., *Artificial Organs*, 11:259–264 (1987); Nilsson, I. M., et al., *In Factor VIII Inhibitors*, p. 225 (1984); Liberti, P. A., et al., *J. Immunol.*, 123:2212–2219 (1979); Randerson, D. H., et al., *Artificial Organs*, 6:43–49 (1982)].

C-reactive protein (CRP) is the prototype acute phase reactant. It was first described by Tillett and Francis in *J. Exp. Med.*, 52:561–571 (1930), who observed that sera from acutely ill patients precipitated with fraction C of the pneumococcal cell wall. Others subsequently identified the reactive serum factor as protein, hence the designation C-reactive protein.

It was later discovered that CRP has a role in host defense. CRP can recognize and bind one of several ligands on the cell or bacterial surface, or in suspension. These ligands include phosphorylcholine, chromatin and polycations. It appears that certain CRP-ligand complexes have the capacity to activate the complement pathway, thus stimulating certain aspects of the immune system.

In clinical use, CRP has been used as a marker of acute inflammation. Its exact role in the body's inflammatory response is not yet known, although it has been shown that injecting mice with liposomes containing C-reactive protein can be effective in inhibiting or reversing certain tumor growth [See Deodhar, S. D., et al., *Cancer Res.*, 42:5084–5088 (1982); Barna, B. P., et al., *Cancer Res.*, 44:305–310 (1984); Thombre, P. S., et al., *Cancer Immunol. Immunother.*, 16:145–150 (1984)].

Under particular experimental conditions, CRP can be altered so as to have charge, size, solubility and antigenicity characteristics significantly different than the CRP molecule monitored as a marker of acute inflammation [See Potempa, L. A., et al., *Mol. Immunol.* 20:1165–1175 (1983)]. The distinctive antigenicity associated with altered CRP has been referred to as "neo-CRP," and the altered CRP molecule itself has been referred to as "modified-CRP." Using appropriate reagents and assays, it has been determined that modified-CRP expressing neo-CRP antigenicity functioned in vitro in a variety of assays used to assess the state of the immune system reactivity. In brief, modified-CRP was found to:

stimulate glass-adherent monocytes to secrete interleukin 1;

stimulate glass-adherent monocytes to increase prostaglandin and leukotriene metabolites;

stimulate glass-adherent monocytes to increase a lymphoblastogenesis response to autologous lymphocytes;

stimulate platelets to aggregate and secrete granular constituents;

potentiate polymorphonuclear leukocytes and monocytes to in crease oxidative metabolism stimulated by aggregated (complexed) immunoglobulins; and stimulate endothelial cells to proliferate and synthesize proteins.

[See Potempa, L. A., Gewurz, H., Harris, J. E., and Braun, D. P., *Protides of the Biological Fluids*, Vol. 34, pp. 287–290 (1986); Potempa, L. A., Zeller, J. M., Fiedel, B. A., Kinoshita, C. M. and Gewurz, H., *Inflammation*, 12:391–405 (1988); Gupta, R. C., Potempa, L. A., Krishnan, M. R., and Postlethwaite, A. E., *Arthritis & Rheumatism*, 31:

R39a (1988); Chu, E. B., Potempa, L. A., Harris, J. E., Gewurz, H., and Braun, D. P., *Amer. Assoc. Cancer Res.* 29: 371a (1988); Doughery, T. J., Zeller, J. M., Potempa, L. A., Gewurz, H., and Siegal, J., *Protides of the Biological Fluids*, Vol. 34, pp. 291–293 (1986)].

The exact mechanism by which modified-CRP contributes to these activities is unknown. However, a consistent feature common to all these listed activities is that modified-CRP either mimics or enhances those activities stimulated by aggregated immunoglobulin.

Also, modified-CRP has also been used in vivo. Mice injected with modified-CRP 30 min. prior to receiving a lethal dose (90%) of type 7F *Streptococcus pneumoniae* survived death in a significant and dose-related manner [See Chudwin, D. S., et al., *J. Allergy Clin. Immunol.*, 77:216a (1986)].

Using appropriate reagents and techniques to identify the natural occurrence of modified-CRP as the neo-CRP antigen on body cells, it has recently been determined that neo-CRP antigenicity is found as a natural component on the surface of large granular lymphocytes (i.e., natural killer (NK) cells, B lymphocytes, polymorphonuclear leukocytes and monocytes). On natural killer and B-cells, the antigen recognized by antibody to neo-CRP has been found to be directly associated with the Fc receptors found on either cell. The Fc receptor on natural killer cells is distinctive from the Fc receptor on B-cells, suggesting that CRP may be a common link in the structures of two physically distinct but functionally related molecules [See Unkeless, J. C., et al., *Adv. Immunol.*, 31:247–270 (1981); Perussia, B., et al., *J. Immunol.*, 133:180–189 (1984); Anderson, C. L. and Looney, J. R., *Immunol. Today*, 7:264–266 (1986)].

SUMMARY OF THE INVENTION

The invention comprises a method of binding aggregated immunoglobulin or immune complexes comprising contacting the aggregated immunoglobulin or immune complexes with C-reactive protein modified as described below (modified-CRP). The method may be used to remove aggregated immunoglobulin or immune complexes from fluids by contacting the fluid with modified-CRP and separating the fluid from the aggregated immunoglobulin or immune complexes bound to the modified-CRP. This aspect of the invention is particularly useful for removing immune complexes from the body fluid of a mammal in need thereof, and to remove aggregated immunoglobulin or immune complexes from fluids used in therapeutic (e.g., gamma globulin) or diagnostic (e.g., antibody solutions) procedures. The method may also be employed in assays to detect and quantitate immune complexes. To detect or quantitate the immune complexes, labeled modified-CRP may be used or a labeled component that binds to the modified-CRP or to the immune complexes may be added to allow the immune complexes to be detected or quantitated. Thus, the method of the present invention may be utilized in diagnostic assays, in the therapeutic treatment of disease, and to remove unwanted aggregated immunoglobulin and immune complexes from fluids used in diagnostic or therapeutic procedures.

In particular, the method of the present invention can be used to control adverse immune reactions by binding immune complexes in body fluids (i.e., whole blood, serum, plasma, synovial, cerebrospinal, pleural, or ascites fluids) or in other immunoglobulin-binding or -containing materials. Immunoglobulin-binding or -containing materials may be defined as materials or solutions used for diagnostic tests, therapeutic treatments or for research purposes that bind or contain immunoglobulins. Specifically, these materials may include plasma, serum, monoclonal antibodies, antigens associated with immune complexes, gamma globulin for injection, complement protein or derivatives, proteins associated with clotting mechanisms, i.e., fibrinogen or fibronectin, etc. Generally, except for separation of plasma from blood, no special pretreatment or separation of the fluid material is necessary.

In practicing preferred embodiments of the method of the present invention, a fluid from a mammal containing immune complexes is contacted with a solid support surface coated with fixedly bound C-reactive protein (CRP) which has been isolated and treated in such a way as to express antigenicity which is distinctive from CRP currently quantified for clinical diagnostic purposes. This distinctive antigenicity is referred to as n-CRP or neo-CRP, and the modified-CRP preferred for use in the practice of the invention expresses neo-CRP antigenicity. The fluid containing the immune complexes is passed over, or incubated on, the solid support surface, such as a granular filtration material in a column in an extracorporeal device, a microtiter well or on another suitable surface, so that the immune complexes are adsorbed without appreciable binding of uncomplexed immunoglobulin. In this manner, the immune complexes are immobilized on the solid support surface. The fluid from which the immune complexes have been removed by this treatment may then be returned to the mammal as part of the therapeutic treatment.

One embodiment of the present invention is the use of modified-CRP ex vivo to mimic and improve upon the natural process by which immune complexes are bound. By appropriately immobilizing CRP or modified-CRP on a solid surface, solutions containing immune complexes can be selectively depleted of them. Most methods of immobilizing CRP on a solid surface results in modification of CRP and expression of neo-CRP antigenicity. Surface-immobilized CRP or modified-CRP will be so configured as to optimize its use for both diagnostic and therapeutic purposes.

In diagnostic use, as in standard immunoassays, after the immune complexes are bound by the modified-CRP to the solid support surface, they can be washed thoroughly while remaining bound to the surface. Such washing assures the removal of unbound components which could reduce the accuracy of the immune complex determination. Following removal of the immune-complex-containing sample from contact with the solid support surface, and preferably after washing the surface, the concentration of the immune complex on the surface is determined by a conventional immunoassay technique.

Another embodiment of the present invention comprises the binding of modified-CRP by another molecule which is necessary to, or which may, enhance aggregated immunoglobulin or immune complex binding to the immobilized modified-CRP. Thus, the sensitivity and/or specificity of modified-CRP to bind aggregated immunoglobulin or immune complexes can be enhanced by co-immobilizing modified-CRP with other molecules that also have immunoglobulin binding activity or by immobilizing modified-CRP on surfaces of appropriate hydrophilicity or hydrophobicity or by immobilizing modified-CRP on solid surfaces having linking agents attached thereto.

Gautier, et al., *J. Exp. Med.*, 156:766–777 (1982) reported the effect of the surface charge on immune complex deposition. Alternatively, various peptides such as -lys-ala-asp-trp-tyr-val-asp-gly have been shown to affect the binding of immune complexes to C1q proteins [See Boackle, R. J., et al., *Nature*, 282:742 (1979)]. Polycationic (e.g., poly-lysine or poly-arginine), polyanionic (e.g., poly-glutamic acid or poly-aspartic acid) and nonelectrostatic forces have all been implicated in the interaction of immunoglobulin with other molecules [See Burton, D. R., *Mol. Immunol.*, 22:161–206 (1985)]. Potempa, et al., *J. Immunol.*, 127:1509–1514 (1981) have reported that CRP can bind to polycationic ligands with selectivity.

Therefore, another embodiment of the present invention is to immobilize modified-CRP on a surface which has been treated to express cationic or anionic charges. For example, protamine may be used to precoat a hydrophobic surface. When modified-CRP is then adsorbed onto this cationic surface, superior results have been found in the binding of immune complexes (see Example 9). When modified-CRP is absorbed onto an anionic surface, enchanced binding is also obtained. Alternative surfaces include but are not limited to commercially available ion-exchange resins, specifically derivitized surfaces and various types of microtiter plates.

A further embodiment comprises the use of modified-CRP or CRP bound to a solid surface for removing aggregated immunoglobulins or immune complexes from reagent fluids or from solutions used in therapeutic treatments or diagnostic tests. Such reagents or solutions can include, but should not be limited to, intravenous gamma globulin, monoclonal and polyclonal antibodies, antiserum, affinity purified antibodies, and other isolated blood components such as Factor VIII and genetically engineered proteins.

The invention further comprises a device for removing aggregated immunoglobulin or immune complexes from fluids comprising modified-CRP bound to a solid surface and a means for encasing the solid surface so that the fluid may be contacted with the solid surface.

The invention also comprises a test kit for detecting or quantitating immune complexes comprising a container holding modified C-reactive protein. The modified-CRP may be labeled to allow for the detection or quantitation of the immune complexes or the kit may also include a container holding a labeled component that binds to the immune complexes or to modified-CRP so that the immune complexes can be detected or quantitated.

Another embodiment of the present invention is a method of reducing the levels of immune complexes in a mammal in need thereof comprising administering to the mammal an amount of modified-CRP effective to reduce the levels of immune complexes. The injection of modified-CRP into the body or blood of a mammal increases the relative concentration of modified-CRP in the mammal. Modified-CRP which expresses neo-CRP antigenicity is a natural component found in mammals. As described in Example 10 (see below), modified-CRP in suspension effectively removed heat-aggregated immunoglobulin from solution.

The invention also comprises a method of binding aggregated immunoglobulin or immune complexes comprising contacting the aggregated immunoglobulin or immune complexes with an antibody to the neo-CRP. The aggregated immunoglobulin or immune complexes may naturally contain modified-CRP expressing the neo-CRP antigen or may be allowed to bind it before, or while, being contacted with the antibody to neo-CRP to add to, or increase the level of, neo-CRP antigen bound to the aggregated immunoglobulin or to the immune complexes. The method may be used to detect or quantitate immune complexes, and a test kit for detecting or quantitating immune complexes comprising a container holding antibody to neo-CRP is also provided. A device for removing aggregated immunoglobulin or immune complexes from fluids comprising antibody to neo-CRP bound to a solid surface and a means for encasing the solid surface so that the fluid can be contacted with the solid surface is also part of the invention.

Finally, the invention comprises a method of making modified-CRP, and a method of binding monomeric immunoglobulin comprising contacting the immunoglobulin with modified-CRP or antibody to neo-CRP. Although modified-CRP binds immune complexes to a much greater degree than monomeric immunoglobulin, it does bind some monomeric immunoglobulin believed to be a subclass of immunoglobulin.

DETAILED DESCRIPTION OF THE PRESENTLY PREFERRED EMBODIMENTS

Methods of isolating C-reactive protein (CRP) from natural sources are well known. The CRP utilized herein was isolated from pleural or ascites fluid by calcium-dependent affinity chromatography using phosphorylcholine-substituted Sepharose (an agarose-based resin made by Pharmacia) as described by Volanakis, et al., *J. Immun.*, 113:9–17 (1974) and modified by Potempa, et al., *Mol. Immunol.*, 24:531–541 (1987). In this procedure, the primary affinity column is exhaustively washed with 75 mM Tris-MCl-buffered saline (pH 7.2) containing 2 mM $CaCl_2$ until the absorbance at 280 nanometers was<0.02, and CRP is eluted in 75 mM Tris, 7.5 mM citrate-buffered saline (pH 7.2). This high concentration of Tris significantly reduces non-specifically adsorbed proteins recognized to contaminate affinity-purified CRP preparations. CRP-containing fractions are pooled, diluted 3-fold with deionized-distilled water, adsorbed to DE52 ion exchange resin and eluted using a linear 0.05–0.5 M NaCl gradient. CRP-containing fractions are pooled, dialyzed into 10 mM Tris-HCl-buffered saline (pH 7.2) containing 2 mM $CaCl_2$ and applied to unsubstituted Biogel A 0.5 to remove residual serum amyloid P component (SAP). The final CRP preparations are concentrated to 1 mg/ml using a CRP extinction coefficient (mg/ml) of 1.98. CRP is exhaustively dialyzed in 10 mM Tris-HCl-buffered saline (pH 7.2) containing 2 mM $CaCl_2$, sterile-filtered and stored at 4° C. preparations produce a single Mr 22,000 band on continuous SDS-PAGE electrophoresis. Final CRP preparations are >99% free of principal contaminants SAP and IgG, and >97% free of all other proteins.

CRP may also be prepared using conventional recombinant DNA and fermentation techniques. The gene sequence for CRP is known, and the CRP gene has been cloned. [Lei et al., *J. Biol. Chem.*, 260: 13377–83 (1985)]. Indeed, CRP made by recombinant DNA techniques may prove to be particularly useful since it has been found to express neo-CRP. [Mantzouranis et al., *Pediatric Research*, 18: 260a (1984)].

CRP is a molecule composed of five subunits arranged in cyclic symmetry. When the individual subunits become dissociated or otherwise modified, the CRP changes structure, and a new antigenicity is expressed (i.e., neo-CRP). Ligand binding, solubility and electrophoretic characteristics are also distinct from the unmodified molecule [Potempa, et al., *Mol. Immunol.*, 20:1165–1175 (1983)].

Modified-CRP is defined as CRP altered by suitable methods so that it binds immune complexes, aggregated immunoglobulin and monomeric immunoglobulin as further described herein. It can be prepared by denaturing CRP or by adsorbing CRP to hydrophobic or hydrophilic solid surfaces. Preferably, the neo-CRP antigen is expressed by the modification process. The term "modified-CRP" also includes that form Of CRP found in mammals using reagents specific for neo-CRP, whereby the neo-CRP is formed by an as yet unknown mechanism. Forms of modified-CRP have been also been shown to stimulate various actions of the immune system.

CRP can be structurally modified or denatured by heat, acid, urea-chelation, adsorption to hydrophobic or hydrophilic solid surfaces, or other methods, to express the neo-antigenicity we identify as neo-CRP. When contacting a solid surface such as that found on a polymeric material, the CRP is modified or denatured to express neo-CRP. This form of modified-CRP is one of the preferred embodiments utilized to bind aggregated immunoglobulin or immune complexes.

While CRP is preferably modified or denatured by being immobilized on a solid surface, other methods of modification or denaturation may be utilized to express the neo-CRP antigen. For example, CRP may be treated or contacted with effective amounts of urea and conventional chelation reagents. The preferred chelation reagents include ethylenediaminetetraacetic acid (EDTA), citric acid and heparin. Further, CRP may be modified or denatured by adjusting the pH of the protein to below about 3 or above about 9.

Heating may also cause modification or denaturation of CRP. The use of chelation reagents may be necessary if the CRP preparation contains calcium ions. Heating above 50° C. for an amount of time effective to cause denaturation or modification to express the neo-antigen is preferred. The CRP may then be dialyzed into a buffer solution having a salt concentration preferably at 0.075 M. However, the salt concentration may be above or below this preferred amount.

After CRP is modified, it may be utilized to bind aggregated immunoglobulin or immune complexes. The modified-CRP may be added directly to a fluid containing the aggregated immunoglobulin or immune complexes or may be attached to a solid surface before being contacted with the fluid containing the aggregated immunoglobulin or immune complexes.

With respect to modified-CRP attached to a solid support surface, body fluids may be incubated statically on the immobilized modified-CRP for use in diagnostic assays, or fluids may be passed dynamically across the immobilized modified-CRP in an extracorporeal device for therapeutic treatment, i.e., binding immune complexes. In selecting a solid support surface, consideration should be given to whether modified-CRP will leach off the solid phase surface. If so, the leaching must be minimized.

Examples of solid phase surfaces that may be utilized with the modified-CRP of the present invention include, but are not limited to, agarose based resins, polyacrylamide, polymethyl-methacrylate, polycarbonate, polysulfone, polyacrylonitrile, polyethylene, polypropylene, latex beads, dextran, glass, nylon, polyvinyl alcohol, gels, clay, and cellulose derivatives as well as other polymeric materials, including polystyrene which has been rendered hydrophilic by specialized treatments. Generally, however, any polymeric material may be utilized which does not result in significant leaching off of the modified-CRP from the solid phase surface. The polymeric material may be hydrophilic, hydrophobic, or both. Preferably, however, hydrophilic polymeric material is utilized. A positively charged surface on the polymeric material will enhance the binding activity of the modified-CRP for binding aggregated immunoglobulin or immune complexes as shown in Example 9. Enhanced binding is also obtained using negatively-charged surfaces. However, if a hydrophobic surface is used, such as on a 96-well microtiter plate used in a static system for diagnostic assays, the modified-CRP adsorbed thereon also has the capacity to bind aggregated immunoglobulin or immune complexes.

In an alternate embodiment of the present invention, CRP adsorbed to a solid surface (hydrophobic or hydrophilic) may be utilized to bind aggregated immunoglobulin or immune complexes. When the CRP is adsorbed directly on the solid surface, it will change and express the antigenic neo-CRP, wherein the binding activity is prevalent. CRP so adsorbed has the immune complex and aggregated immunoglobulin binding characteristics of CRP modified prior to adsorption on the solid surface.

Further, modified-CRP can be adsorbed onto the surface of a polymeric material shaped as beads for use in a column, to allow circulating immune complexes to be bound. If CRP is utilized, it will be adsorbed onto the surface of the beads, denatured and unfolded to express the neo-CRP antigen. Column and solid phase materials are commercially available in the United States from Bio Rad Laboratories (Richmond, Calif.); Pierce Chemical Co. (Rockford, Ill.); Pall Biosupport (Glen Cove, N.Y.); Micro Membranes (Newark, N.J.); Pharmacia Fine Chemicals (Uppsala, Sweden); and others.

In an effort to ensure complete binding of aggregated immunoglobulin or immune complexes to modified-CRP, a linking agent may be utilized to secure the attachment of the modified-CRP to polymeric material. The modified-CRP may be immobilized non-covalently or covalently on the surface of the polymeric material with a linking agent. For purposes of this invention, linking agents are incorporated as part of or derivatized onto the polymeric solid surface before the protein is added and are considered conventional, and they may include, but are not be limited to, diimidoesters, carbodiimide, periodate, alkylhalides, dimethylpimelimidate and dimaleimides [See Blair A. H., and Ghose, T. I., *J. Immunol. Methods,* 59:129 (1983); Blair, A. H., and Ghose, T. I., *Cancer Res.,* 41:2700 (1981); Gauthier, et al., *J. ExDr. Mad.,* 156:766–777 (1982)].

Rizk, S. L., et al. in *Cancer,* 58:55–60, Jul. 1, 1986, report that positively charged peptides can fix CRP to target cells. These polycations include poly-L-arginine, histones (nuclear), and protamine and major basic protein (eosinophilic). Linking with polycations has also proved effective for modified-CRP.

It has also been found that a negatively-charged surface enhances binding of aggregated immunoglobulin or immune complexes. Suitable materials useful for preparing such a negatively-charged surface include glycine, aspartic acid, glutamic acid, and heparin. It should be noted that glycine is zwitterionic in solution and will express a negative charge only after being bound to the solid surface through the amine group.

Conjugation reactions generally require an initial modification of protein amino acid R groups or cross linking agent or both. Such modifications may serve to selectively activate R groups (e.g., carbodiimide-O-acyl urea, intermediate formation with aspartic, glutamic, and C-terminal carboxyl residues) to allow for reaction with appropriate available agent functional groups (amino groups in the case of carbodiimide). Modifications can also include the introduction of a new reactive moiety (e.g., N-succinimidyl-3-(2-pyridyldithio)-propionate) which introduces pyridyldithio groups on lysine epsilon-amino residues. This allows for disulfide bond formation between protein and agent. In some cases, bifunctional coupling reagents are employed which form bridges between the protein R groups and the agent of interest.

Modified-CRP of the present invention can be used to remove aggregated immunoglobulin immune complexes from fluids such as whole blood, plasma, other body fluids, or other immunoglobulin-binding or containing materials, by simply contacting the fluid with the modified-CRP. Such contact can be effected by passing the blood, plasma or other fluid through an extracorporeal device having a solid surface coated with modified-CRP and a means for encasing the solid surface so that the fluid may contact the solid surface. The duration of the contact is not bound to critical limits although it should, of course, be sufficient to allow aggregated immunoglobulin or immune complexes to be adsorbed to and bound by modified-CRP on the solid surface.

For therapeutic uses, CRP or appropriately modified CRP can be coated on a solid support surface which is encased online in an extracorporeal device through which whole blood or plasma can be circulated dynamically so that the immune complexes contained therein are bound and thereby removed from the plasma or blood. This process could be used with conventional plasmapheresis or hemodialysis techniques. Such fluids can be returned to the body negating the need for blood replacement therapy.

The solid surface and encasing means of the device may be made of any biocompatible material. For instance, the solid surface may be a membraneous surface, agarose-based beads or hollow fibers coated with modified-CRP. The extra-corporeal device may be a column packed with beads, a hollow fiber membrane encased in a cylinder like those used in renal dialysis, a microtiter plate containing wells, or any suitable surface, coated with modified-CRP. The device may also include appropriate tubing for connecting it to a patient and a pump to aid the passage of the fluid through the device and back into the patient and to prevent air from entering the system. The device must be sterilized for therapeutic use, and sterilization may be accomplished in conventional ways such as purging with ethylene oxide or by irradiating the device.

The invention also comprises a method of detecting or quantitating immune complexes comprising contacting the immune complexes with modified-CRP so that the immune complexes bind to the modified-CRP. The modified-CRP may be added directly to fluids containing the immune complexes or may be immobilized on a solid surface of the types, and in the ways, described above. The modified-CRP may also be added directly to cells or a tissue sample having immune complexes thereon, and labeled modified-CRP may be injected into a mammal so that it localizes in areas of the mammal's body where immune complexes are found, such as areas of inflammation.

In diagnostic assays, modified CRP can be directly added to solutions containing immune complexes to bind and alter the immune complexes and to change the immune complex properties so as to enhance the precipitation of the immune complex and to enhance other binding interactions of the immune complexes leading to immune complex removal from circulation. Alternatively, CRP or appropriately modified CRP can be immobilized on a solid support surface so that fluids containing immune complexes or immunoglobulins may be contacted therewith, or incubated and, after washing to remove non-specifically bound immunoglobulins, if desired, the bound immune complexes can be detected or quantified.

To detect or quantitate the immune complexes, labeled modified-CRP can be used. The labels useful in the invention are those known in the art such as $I^{125}$, biotin, enzyme or fluorescent labels. Alternatively, the immune complexes can be detected or quantified using conventional immunoassay techniques by adding a labeled component that binds to the immune complexes or the modified-CRP. Such conventional immunoassay techniques include agglutination, radioimmunoassay, enzyme immunoassays and fluorescence assays. Enzyme-linked immunosorbent assays (EIA) are preferred since they provide a means for sensitive quantitation of levels of immune complexes.

The EIA utilized in the examples herein is a standard EIA assay performed as follows. One hundred microliters of test protein (1–10 micrograms/ml) are placed in each well of polystyrene plates and incubated for 2 hr at 37° C. For EIA analyses in which CRP or modified-CRP was directly immobilized, CRP or modified-CRP was dialyzed or diluted in 10 mM sodium bicarbonate buffer (pH 9.0) prior to coating. Similar results were obtained when CRP or modified-CRP was prepared in phosphate buffer at pH 7.4. Wells were washed with 10 mM phosphate buffer (pH 7.3), containing 0.3 M NaCl and 0.05% Tween-20 (wash buffer), before being backcoated with 1% bovine serum albumin (BSA) in water for 30 min at 37° C. and rinsed with wash buffer. Test samples (100 microliters/well) were diluted in 0.1 M phosphate-buffered saline (pH 7.3) (PBS), containing 1% BSA, and were allowed to incubate for 1 hr at 37° C. After multiple washing steps, 130 microliters of appropriate enzyme conjugate, diluted in 0.02 M PBS containing 1% BSA was added and incubated for 2 hr at 37° C. After washing, 100 microliters of enzyme substrate solution was added per well and incubated at 37° C. Wells were read for absorbance at appropriate wavelengths on a Titertek multiskan plate reader (Flow Laboratories, Helsinki, Finland).

Modified-CRP may also be coated onto latex beads for use in agglutination assays or onto dipsitcks made of, e.g., polycarbonate, polysulfone or latex, for use in qualitative or semi-quantitative immunoassays. In general, any immunoassay technique can be used that results in an observable change in properties.

The labeled components added to the immune complexes bound to the modified-CRP to allow for the detection or quantitation of the immune complexes are conventional reagents used in immunoassays. Also, the labels used are those known in the art. For instance, enzyme-labeled, $I^{125}$-labeled or biotin-labeled antibodies to the immunoglobulin or the antigen in the immune complexes could be used.

Since body fluids from mammals normally contain immune complexes, comparison of the levels of immune complexes in a test sample from a mammal will have to be made to the levels found in normals to identify levels of immune complexes indicative of a disease state.

A test kit for detecting or quantitating immune complexes is also part of the invention. The kit comprises a container holding a solution of modified-CRP or modified-CRP attached to a solid surface. The solid surfaces are the types described above, and the modified-CRP is attached as described above. Thus, the container could be a bottle holding a solution of modified-CRP, a dipstick coated with modified-CRP encased in a protective package, a bottle holding latex beads coated with modified-CRP or a microtiter plate, the wells of which are coated with modified-CRP.

The modified-CRP may be labeled if it is to be used for detecting or quantitating the immune complexes. Alternatively, the kit may further comprise a container holding the above-described labeled component that allows for the detection or quantitation of the immune complexes when an immunoassay technique is used.

Fragments derived from CRP or modified CRP, which may or may not express the neo-CRP antigenicity, may have the biological functionality of the modified CRP. These fragments may be peptides. Thus, the invention also contemplates the use of any such fragments that bind immune complexes or aggregated immunoglobulin.

Antiserum and polyclonal or monoclonal antibodies formed by conventional techniques to neo-CRP or to peptide fragments of CRP may also be used for binding aggregated immunoglobulin or immune complexes. Preferably, CRP may be denatured or modified as described above, and antibodies may then be formed against the neo-CRP antigen by conventional techniques. A method of dissociating CRP and of isolating and characterizing CRP antigen is disclosed in Potempa, et al., *Mol. Immunol.* 24:531–541 (1987), which is incorporated herein by reference.

The antibodies to neo-CRP may then be used to bind aggregated immunoglobulin or immune complexes which may naturally contain CRP expressing the neo-CRP antigen. Alternatively, the immune complexes or aggregated immunoglobulin may be contacted with modified-CRP expressing the neo-CRP antigen before, or while, being contacted with the antibody to neo-CRP to add to, or to increase the level of, neo-CRP antigen bound to the aggregated immunoglobulin or immune complexes.

This method may be used to detect or quantitate immune complexes in fluids, on cells or on tissues, and a test kit comprising a container holding antibody to neo-CRP and, optionally, a container holding modified-CRP that expresses neo-CRP is also provided. The antibody to neo-CRP may be labeled with known labels (e.g. labeled with $I^{125}$, enzyme, biotin, fluorescein) to allow for detection and quantitation of the immune complexes. Alternatively, a labeled component that binds to the immune complexes or to the antibody to neo-CRP may be used to detect or quantitate the immune complexes, and the kit may further comprise a container holding this component. Again, these labeled components and the labels are those known for use in immunoassays.

A device is also provided for removing aggregated immunoglobulin or immune complexes from fluids comprising antibody to neo-CRP bound to a solid surface and a means for encasing the solid surface so that the fluid can be contacted with the solid surface. Methods of binding antibody to solid surfaces are known. Otherwise, the construction, operation and utility of this device are the same as the device described above having modified-CRP bound to a solid surface.

When used independently without a solid surface for support, modified-CRP may still bind immune complexes in a fluid phase interaction. Thus, modified-CRP, selected biologically active portions of modified-CRP, or CRP may be injected into a body fluid for therapeutic activity against cancer and other diseases. Upon introduction of modified-CRP into the body fluid containing the immune complex, the soluble antigen and antibody complex may grow larger in physical size and may precipitate (fall out of solution) or may be otherwise modified to enhance their removal by phagocytes. Zahedi, et al., *Cancer Res.* 46:5077–5083 (1986) and Barna, et al., *Cancer Res.* 47:3959–3963 (1987) have shown that macrophages and monocytes are stimulated to increase anti-cancer responses in the presence of CRP. The present invention discloses a therapeutic effect of modified-CRP by promoting precipitation as shown in Example 10.

In laboratory practice, modified-CRP may be used to remove aggregated immunoglobulin or immune complexes from fluids used for research or in therapeutic procedures or diagnostic tests. The presence of aggregated immunoglobulin in such reagents may be expected because of processing steps used to make these fluids, such as heat treatment of antisera to inactivate complement. The modified-CRP or CRP may be bound on a solid surface for binding aggregated or complexed immunoglobulins from reagent material or solutions, e.g., solutions containing monoclonal antibodies, derivitized reagents, intravenous gamma globulin, or isolated blood components. Alternatively, the modified-CRP may be added directly such reagent materials or solutions in order to bind aggregated or complexed immunoglobulins, thereby rendering them non-detrimental.

As shown in the following examples, modified-CRP also binds to monomeric immunoglobulin, although to a much lesser degree than it binds to aggregated immunoglobulin or to immune complexes. By sequentially passing normal plasma over columns of agarose beads to which modified-CRP is bound, it has been found that about 5% of the monomeric immunoglobulin is removed by the first column, about 1% is removed by the second column, and less than 1% is removed by the third column. Thus, only a selected portion or subclass of immunoglobulin binds, not monomeric immunoglobulin in general. This subclass of immunoglobulin has not yet been characterized, but may be abnormal immunoglobulin and may be associated with a disease state. Thus, the method of the present invention will be useful in characterizing this subclass of immunoglobulin and may be used to quantitate and remove this material from fluids and to monitor and treat any such disease state.

The methods of binding, quantitating and removing this subclass of immunoglobulin are the same as already discussed for the binding, quantitating and removing of immune complexes using modified-CRP and antibody to neo-CRP. Also, kits and devices like those already described could be employed to detect and quantitate this immunoglobulin and to remove it from fluids.

EXAMPLES

The methods of this invention are further illustrated by the following examples.

Example 1

Preparation of molecules presenting the CRP neo-antigen using urea and chelation Purified CRP (1 mg/ml) (prepared as described above) was incubated in 8 M ultra-pure urea (Schwartz-Mann, Spring Valley, N.Y.) in the presence of 10 mM EDTA for 1 hr at room temperature. These conditions are found to be optimal for the generation of neo-CRP as described in Potempa, et al., *Mol. Immunol.*, 20:1165–1175 (1983). When urea was removed by dialysis in 10 mM phosphate buffer (pH 7.4) containing 0.15 M NaCl, most of the CRP precipitated. About 100–150 micrograms/ml CRP remained soluble as quantified by both extinction coefficient and the Lowry protein assays. Using electrophoretic and antigenic detection methods, the neo-CRP antigen was found in both precipitated and soluble fractions. When urea was removed by dialysis into 10 mM phosphate buffer (pH 7.4) containing 0.015 M NaCl, no visible precipitate was observed; >90% of the protein available prior to treatment was accounted for in the solution phase after dialysis.

Example 2

EIA Binding of Immune Complexes of Varying Antibody-Antigen Ratios by Modified-CRP Rabbit anti-peroxidase antiserum and isolated peroxidase enzyme were pre-incubated together at various ratios in the presence of 6.25% rabbit serum to form soluble immune complexes (sol-ICs). Rabbit serum was centrifuged before use to minimize the effect of any endogenous complexed or aggregated immunoglobulins (Igs) present. Reagent ratios were adjusted to form ICe of approximately 5:1, 2.5:1 and 1.25:1 antibody (Ab):enzyme(Enz) ratios (mole:mole). Serum containing anti-peroxidase:peroxidase sol-ICs was incubated in the wells of polystyrene 96-well microtiter plates to which modified-CRP (prepared as described in Example 1) had been immobilized at 10 micrograms/ml by conditions defined previously. This assay construct allowed direct development of the EIA for bound complex with peroxidase substrate thus avoiding the need for another washing and incubation step. As controls, surface-immobilized BSA (negative control) and Staphlococcal protein A (positive control) were utilized for comparisons of binding to surface-immobilized modified-CRP. In all cases, enzyme alone, added to normal rabbit serum, did not bind to any experimental surfaces. The following results were obtained.

TABLE 1

Absorbance at 414 nm measuring binding of rabbit anti-peroxidase to modified-CRP

| Approx Ab:Enz molar ratio | Ab Alone followed by Enz alone | Sol-ICs | Ratio of enhanced binding of Sol-IC/Ab Alone |
|---|---|---|---|
| 5:1 | 0.23 | 0.50 | 2.2 |
| 2.5:1 | 0.10 | 0.46 | 4.6 |
| 1.25:1 | 0.005 | 0.87 | 174.0 |

These data indicate modified-CRP does bind sol-IC from 2.2 times to 174 times greater than antibody alone. ICs containing 1 to 3 antibodies per antigen were most notably differentiated from free antibody binding. Sol-ICs were also found to bind protein A at all ratios described here. However, up to 66 times more uncomplexed immunoglobulin bound to Protein A than to modified-CRP (at the 1.25:1 ratio). Thus, protein A is less selective in binding monomer immunoglobulin than immunoglobulin in ICs. Similar experiments were performed using rabbit anti-peroxidase reagents which were affinity purified, using a rabbit anti-β-galactosidase-β-galactosidase antibody:enzyme system, and using a goat anti-biotin (also affinity purified) -biotinylated alkaline phosphatase system. In all systems, the experimental results were essentially the same as those shown.

Example 3

Sensitivity of immobilized modified-CRP to bind ICs

Affinity-purified antibody systems similar to those described in Example 2 were adjusted to 2.5:1 ratio of antibody to enzyme. Specific amounts of sol-ICs were added to either buffer containing 1% BSA or diluted normal serum (6.25%). The amount of immobilized modified-CRP (modified as described in Example 1) was varied from 10 microgram/well to 1 nanogram/well, and numerous sigmoidal binding curves of sol-IC offered to and bound by modified-CRP were established. 0.5 to 1 microgram modified-CRP/well was optimal for EIAs with as little as 50 to 100 nanogram/well being functional under certain assay conditions and sol-IC concentrations.

The assay construct could detect from 1 to 10 micrograms antibody protein present as sol-ICs. Goat and rabbit antibodies, as sol-ICs, selectively bound to modified-CRP. Additional inhibition experiments using sol-ICs of rabbit and goat antibodies showed that there was no apparent species specificity exhibited in their binding to modified-CRP.

Example 4

Binding of human immunoglobulin aggregates to modified-CRP

Since no defined human immune complex system was readily available, isolated human immunoglobulin (Ig) which was biotinylated as a control system was utilized. EIAs were performed as described in Examples 2 and 3 utilizing 1 microgram/well levels of modified-CRP immobilized on polystyrene surfaces. Biotinylated Ig was heat-aggregated for 30 min at 63° C. (agg Ig), and large complexes were removed by centrifugation. Heat-aggregated biotinylated Ig was diluted to the indicated concentrations and incubated on immobilized modified-CRP for 1 hr. Non-bound material was removed by multiple washing steps, and bound Ig was detected using Streptococcal-avidin-β-galactosidase-enzyme conjugate and appropriate substrate.

TABLE 2

Absorbance @ 405 nm measuring binding of biotinylated-human IgG

| Micrograms Ig/ml | on modified-CRP | | on Protein A | | on Clq | |
|---|---|---|---|---|---|---|
| | Monomer Ig | Agg Ig | Monomer Ig | Agg Ig | Monomer Ig | Agg Ig |
| 120.0 | 0.40 | 0.74 | 0.50 | 0.91 | 0.86 | 0.72 |
| 60.0 | 0.37 | 0.52 | 0.63 | 0.63 | 0.74 | 0.75 |
| 30.0 | 0.24 | 0.52 | 0.66 | 0.82 | 0.73 | 0.66 |
| 15.0 | 0.16 | 0.42 | 0.66 | 0.92 | 0.68 | 0.73 |
| 7.5 | 0.10 | 0.25 | 0.72 | 0.82 | 0.61 | 0.65 |
| 3.75 | 0.05 | 0.15 | 0.72 | 0.72 | 0.46 | 0.60 |
| 1.87 | 0.03 | 0.09 | 0.78 | 0.68 | 0.34 | 0.48 |
| 0.94 | 0.01 | 0.05 | 0.61 | 0.50 | 0.24 | 0.38 |
| 0.47 | 0 | 0.02 | 0.37 | 0.28 | 0.14 | 0.22 |

These data indicate that modified-CRP does bind human agg Ig with similar sensitivity to protein A and Clq. Further, from this experiment, modified-CRP appears to be a superior reagent in that it binds much less monomeric Ig than either protein A or Clq. A clear distinction between monomer Ig and agg Ig binding to modified-CRP is observed at Ig concentrations from approximately 2 micrograms/ml to 50 micrograms/ml (see underscored values in Table 2). If one were to calculate that sol-ICs which would be expected to be present in normal human serum (NHS) accounted for 0.001 to 1% of total Ig (estimated to be 10 mg/ml), sol-IC detection assays require sensitivities of from 0.5 micrograms/ml to 100 micrograms/mi. Thus, modified-CRP functionally differentiates sol-ICs in this concentration range more efficiently than the other reagents tested.

Example 5

Inhibition EIA to identify and quantitate modified-CRP binding factors in sera

Various dilutions of sara were incubated on modified-CRP (prepared as described in Example 1) immobilized at 1 microgram/well on polystyrene microtiter plates to allow binding of ICs. After washing, it is anticipated that there may be some changes (i.e., an anticipated decrease) in the binding of a specifically prepared anti-neo-CRP-enzyme conjugate reagent, the rationale being that the ICs bound to the modified-CRP will block access of binding of anti-neo-CRP poly- and monoclonal antibodies (and appropriate enzyme-conjugates) to the neo-CRP antigen. Two results were obtained: 1) A serum factor, presumably ICs, did bind to the solid-phase-adsorbed modified-CRP as detected with enzyme-conjugated anti-human IgG reagent in separate assay wells; and 2) The IgO bound to modified-CRP was not reactive with enzyme-conjugated protein A. This latter finding suggests that the IgG was binding to modified-CRP in a way which blocks the binding of protein A to the C 2-C 3 switch region of IgGs [See Burton, D. R., *Mol. Immunol.*, 22:161–206 (1985); Sjodahl, *J. Eur. Biochem.*, 78:471–490 (1977)].

Comparable results were obtained using modified-CRP prepared by direct immobilization on the wells of the microtiter plates instead of modified-CRP prepared by urea-chelation.

Example 6

Figure 1:
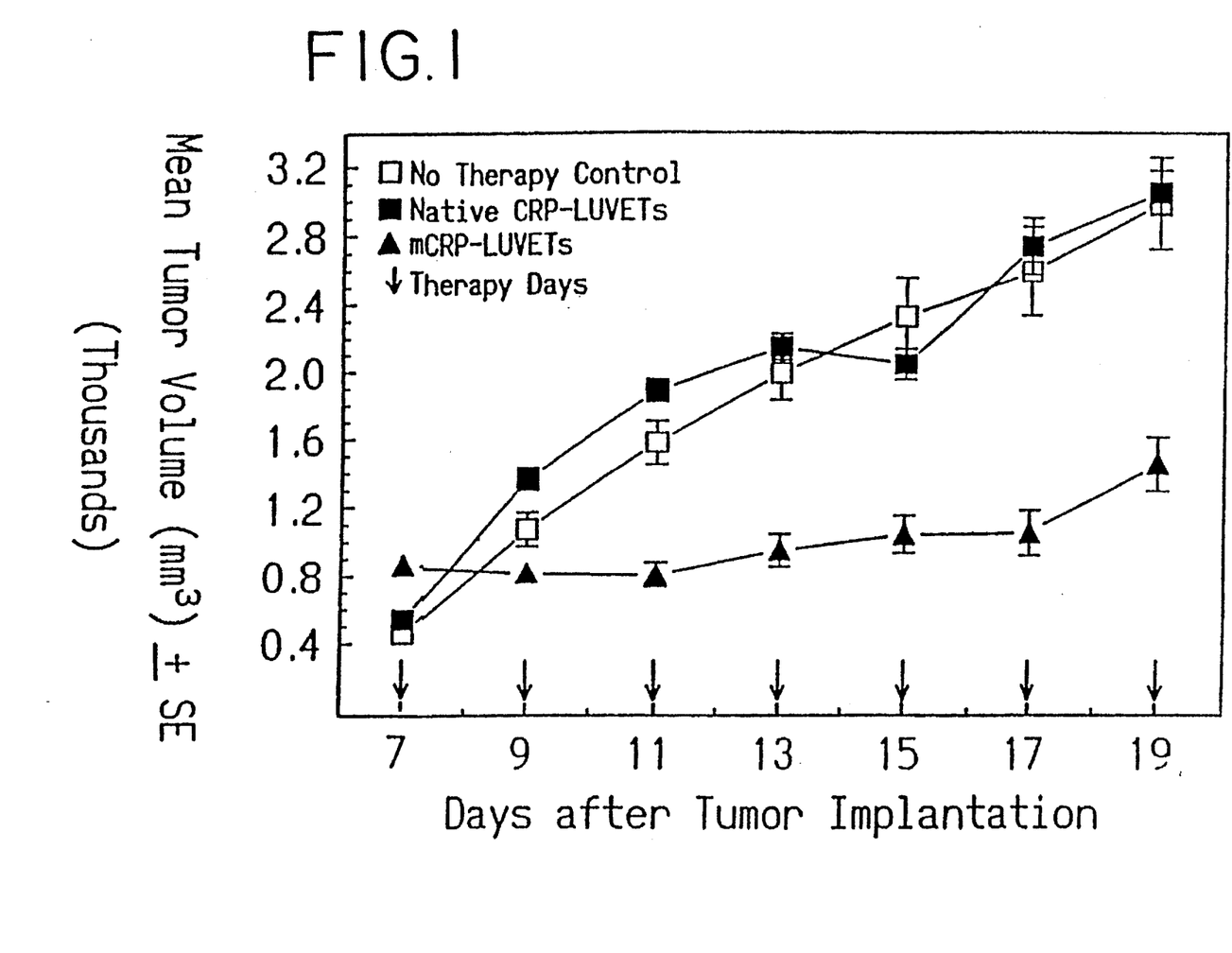
FIGS. 1–3 show binding of immunoglobulin from diseased and normal (i.e., various negatives) human sera to modified-CRP immobilized on polystyrene microtiter wells.
Figure 2:
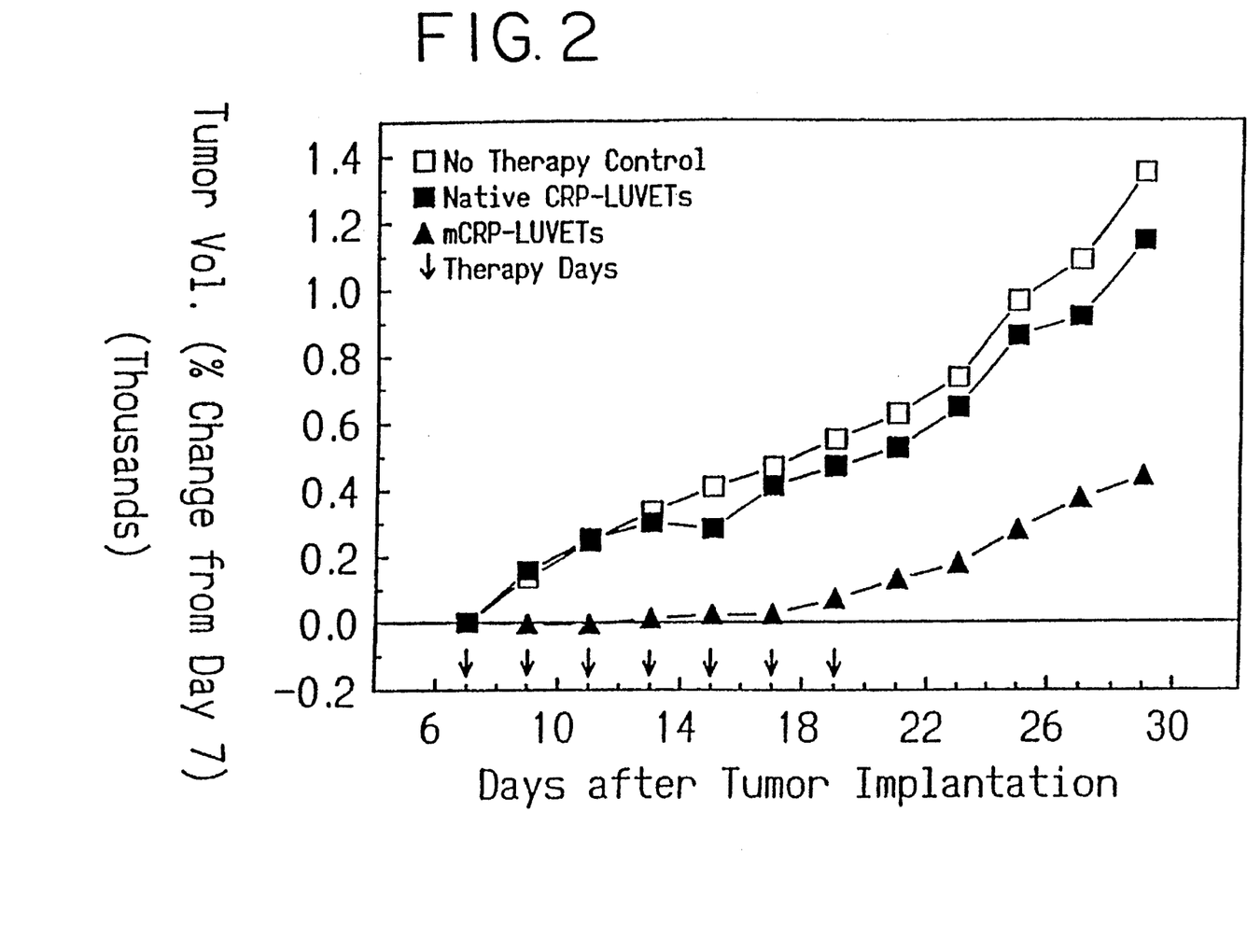
Figure 3:
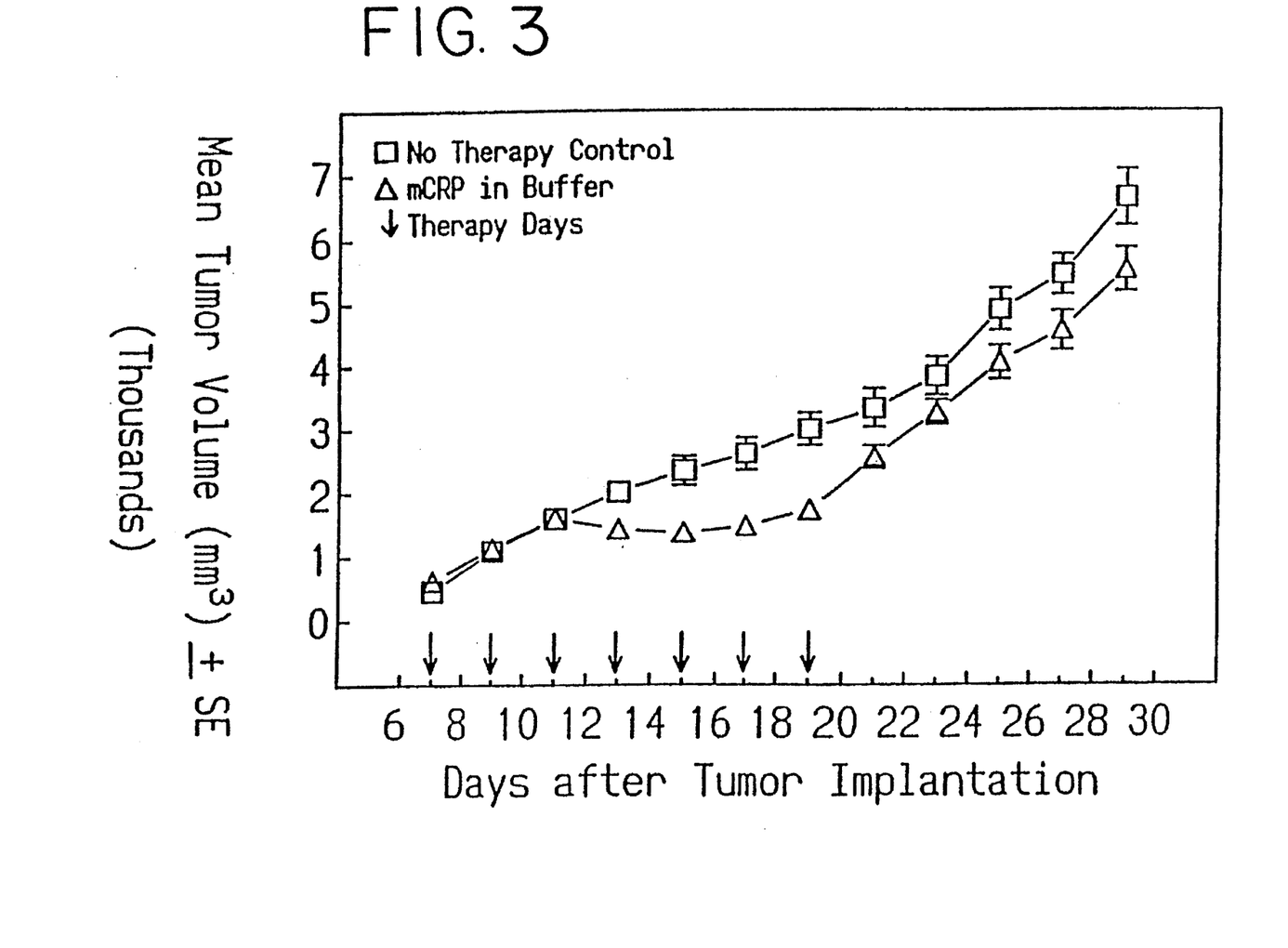

Binding of immune complexes from patient sera, plasma and pleural fluids to modified-CRP Sera, plasma, and pleural fluids from 21 patients with various diseases were tested for human IgG (using enzyme conjugated anti-human IgG reagent) binding to modified-CRP, prepared as described in Example 1. We found binding material in 17 of the 21 samples (81% positive). In general, plasma samples gave identical, or in some cases enhanced amounts of modified-CRP binding material compared to sara. As in the case of modified-CRP binding material previously described, the IgG which bound was not detectable with protein A developing reagents. For the 10 normal human sara tested, low amounts (negatives in the graphs) of IgG were detected and only at 1:10 or less dilution of sara. Examples of EIA binding curves are shown in FIGS. 1–3.

In general, two patterns were observed. One result is illustrated with sara from patients with rheumatoid arthritis (FIG. 1) or appendicitis (FIG. 2). The amounts of IgO material which bound to modified-CRP correlated with the serum concentration (serum dilution). The second type of result is illustrated with sara from patients with temporal arteritis (FIG. 1 or 2) or appendicitis (FIG. 3). Bell-shaped curves were obtained suggesting a prozone-like phenomenon. The levels of IgG bound to modified-CRP were much greater in patient samples (being observed at up to 1:1000 dilution) than in normal serum samples. We did not find either a positive or inverse correlation of the levels of modified-CRP binding IgG and the serum levels of CRP. Thus, whereas CRP is used as a general index of inflammation, its levels do not apparently reflect on modified-CRP's capacity to bind presumably complexed IgG.

Comparable results were obtained using modified-CRP prepared by direct immobilization on the wells of the microtiter plates instead of modified-CRP prepared by urea-chelation.

Example 7

Binding of Igs from sera containing rheumatoid factor activity to modified-CRP

We incubated patient sera known to have rheumatoid factor, as measured by the latex agglutination test, on solid-phase immobilized modified-CRP (prepared as described in Example 1). Assay conditions were identical to those defined in previous examples. After washing, wells were probed for bound IgM and IgG using anti-human-IgM and anti-human-IgG enzyme conjugates. Normal human sera were used as controls. All samples were precentrifuged in an airfuge to remove particulate complexes prior to plate incubation. The following was observed:

TABLE 3

| | Agglutination titer | Absorbance @ 405 nm measuring binding to modified-CRP of | | | | | |
|---|---|---|---|---|---|---|---|
| | | Human-IgM Dilution | | | Human-IgG Dilution | | |
| | | 1:10 | 1:20 | 1:40 | 1:10 | 1:20 | 1:40 |
| Normal Serum #1 | — | 0.01 | 0.01 | 0.01 | 0.04 | 0.04 | 0.03 |
| Normal Serum #2 | — | 0.02 | 0.02 | 0.01 | 0.10 | 0.08 | 0.07 |
| Patient #1 | 1:560 | 0.23 | 0.20 | 0.14 | 0.39 | 0.40 | 0.36 |
| Patient #2 | 1:340 | 0.08 | 0.07 | 0.07 | 0.38 | 0.34 | 0.28 |
| Patient #3 | 1:220 | 0.04 | 0.04 | 0.03 | 0.28 | 0.27 | 0.20 |

These data indicate that IgG from rheumatoid arthritis patient sera bound to modified-CRP, and IgM from at least one of the sera also bound to modified-CRP (see underscored values in Table 3). No IgM and only a small amount of IgG bound from the two normal sera. The level of detected IgG or IgM bound decreased as serum was diluted to the 1:40 level. These data are consistent with the previous results that show modified-CRP can bind ICs in a great excess of monomeric Igs.

Example 8

Demonstration that Modified-CRP Binds Aggregated IgM and Aggregated IgA as well as Aggregated Purified-biotinylated human IgG (Vector Laboratories, Burlington, Calif.) and chromatographically purified IgM and IgA preparations (Jackson Immune Research Laboratories, Avon Park, N.Y.) biotinylated by standard protocols were used. Aliquots of each conjugate were heat aggregated by incubation in a 63° C. water bath for 25 min. Both heat-aggregated and non-heat-aggregated aliquots were centrifuged at 140,000×g for 10 min to remove large, insoluble aggregates. The resultant supernatant fluids were quantified by absorbance at 280 mm and used immediately.

Polystyrene EIA plates were coated with 100 microliters/well of a 10 microgram/ml solution of modified-CRP (prepared as described in Example 1) in 0.1 M. sodium bicarbonate (pH 9.4) overnight at 4° C. Wells were aspirated and backcoated with 1% bovine serum albumin (BSA) in phosphate buffered saline (pH 7.3) (PBS), containing 0.02% sodium azide for 1 hr. at 37° C. Wells were aspirated and extensively washed in PBS containing 1% BSA, 0.02% sodium azide and 0.1% Tween 20 (wash buffer) before 100 microliter/well dilutions of aggregated and non-aggregated, centrifuged, biotinylated immunoglobulins were incubated in wells coated with modified-CRP for 1 hr. at 37° C. Wells were aspirated and extensively washed with wash buffer before 100 microliter/well of a dilution of Streptococcal-avidin-β-galactosidase conjugate (Life Technologies, Inc., Gaithersburg, Md.) in wash buffer was added per well and incubated for 1 hr. at 37° C. Wells were aspirated and extensively washed in wash buffer, and 100 microliters/well of the enzyme substrate ortho-nitrophenyl-β-galactopyranoside at 4 mg/ml in substrata buffer (PBS) containing 5 mM magnesium chloride and 0.78% β-mercaptoethanol was added. The reaction was quantified by absorbance change at 405 nanometers after incubation for 10 to 120 min at ambient temperatures. The results are summarized as follows:

TABLE 4

| Concentration of Ig incubated on Modified-CRP (microgram/ml) | Absorbance Class of Ig | | | | | |
|---|---|---|---|---|---|---|
| | IgG | | IgM | | IgA | |
| | monomer | aggregate | monomer | aggregate | monomer | aggregate |
| 30 | 0.220 | 0.466 | 0.089 | 0.929 | 0.395 | 0.923 |
| 15 | 0.117 | 0.255 | 0.047 | 0.669 | 0.212 | 0.686 |
| 7.5 | 0.059 | 0.129 | 0.027 | 0.397 | 0.100 | 0.407 |
| 3.75 | 0.029 | 0.079 | 0.014 | 0.216 | 0.053 | 0.225 |

These results indicate that modified-CRP binds each of IgG, IgM and IgA aggregates from 3 to 10 times better than modified-CRP binds monomeric Ig. As all three Ig classes have been shown to be naturally present in ICs, these data indicate modified-CRP is effective in binding ICs of all Ig classes.

Example 9

Effect on binding of monomer and aggregated IgG of precoating the surface to which modified-CRP is adsorbed with hydrophilic ligands Polystyrene EIA plates were coated with 100 microliters of various concentrations of protamine (a polycationic ligand) overnight at 4° C in 0.1 M sodium bicarbonate (pH 9.4). After aspiration, 100 microliters of modified-CRP (prepared as described in Example 1) at 100 micrograms/ml were added and incubated for 2 hr. at 37° C. in 0.1 M sodium bicarbonate buffer (pH 9.3). After aspiration, wells were back-coated with 1% BSA in PBS containing 0.02% sodium azide for 1 hour at 37° C. Wells were aspirated and washed extensively in wash buffer and 100 microliters of monomer or heat aggregated biotinylated human IgG at 15 micrograms/ml, prepared as described in Example 8, were added in wash buffer and incubated for 1 hr. at 37° C. After aspiration and extensive washing, an aspirated dilution of Streptococcal-avidin-β-galactosidase conjugate was added and incubated for 1 hr. at 37° C. After aspiration and washing, ortho-nitro-phenyl-β-D-galactopyranoside was added and reaction recorded exactly as described in Example 8.

Results are summarized as follows:

TABLE 5

Absorbance @ 450 nm Indicating Binding of IgG to Modified-CRP

| Form of IgG | Adsorbed directly to latex surfaces | Adsorbed to BSA coated surface | Adsorbed to protamine coated surfaces at protamine concentrations of (micrograms/well) | | | |
|---|---|---|---|---|---|---|
| | | | 1.0 | 0.5 | 0.25 | 0.125 |
| Monomer IgG | 0.204 | 0.145 | 1.181 | 0.769 | 0.281 | 0.205 |
| Aggregated IgG | 0.443 | 0.323 | >2.0 | 1.726 | 0.838 | 0.573 |

These results indicate that modified-CRP, when immobilized on a polycationic surface, retains its capacity to bind aggregated (complexed) IgG and, in addition, bind from 1.3 to at least 4.5 times more agg IgG than modified-CRP directly immobilized on the polystyrene plate surface. Comparable results have been obtained when glycine, aspartic acid and glutamic acid were immobilized on solid surfaces and when heparin was coated onto solid surfaces. These data suggest the efficiency with which modified-CRP binds IC is enhanced when modified-CRP is immobilized on specially prepared surfaces.

Modified-CRP did adsorb to BSA coated surfaces and retained preferential binding activity for aggregated Ig. However, the efficiency by which modified-CRP bound aggregated IgG was not improved over that level measured by the binding of modified-CRP directly adsorbed to the poly-styrene plate surface.

Example 10

Effect of adding modified-CRP to solutions containing monomer or aggregated human IgG Human IgG (Immune Serum Globulin, Cutter-Gamastan) was prepared at 1 mg/ml in 10 mM phosphate, 0.3M sodium chloride (pH 7.3). An aliquot was heated for 30 minutes at 63° C. in a water bath. Modified-CRP prepared from isolated CRP by urea-chelation as described in Example 1 (8M urea, 10 mM EDTA, 1 hr. at 37° C., dialyzed into PBS) was added to either unheated or heat-aggregated IgG. Modified-CRP under these conditions predominantly precipitates; therefore, a suspension of modified-CRP was made and added to IgG (monomer IgG or heat aggregated IgG) aliquots so that the final modified-CRP concentration was approximately 100 micrograms/ml. The modified-CRP-IgG mixture was incubated for 1 hr. at 37° C. after which samples were centrifuged for 30 min. at 10,000×g to remove precipitate. Supernatants were decanted and concentrations of protein remaining soluble were calculated by absorbance at 280 nm.

Corrections were made for the maximal amount of absorbance additionally contributed to the mixture by modified-CRP which remained soluble in PBS under identical treatments.

Under these conditions, no decrease in IgG concentrations was observed when monomer IgG (unheated) was mixed with modified-CRP. When heat aggregated IgG was mixed with modified-CRP, 34.9% of the aggregated IgG was removed from solution. These data indicate that modified-CRP can enhance the precipitation of aggregated (complexed) IgG in the fluid phase.

Example 11

Preparation of anti-neo-CRP serum and affinity purified anti-neo-CRP antibodies

Conventional processes for preparing antiserum can be utilized. However, in order to optimize the expression of the neo-CRP antigen, it is necessary to immunize with urea-chelated CRP.

Monospecific antiserum to neo-CRP is prepared in goats using the following procedure. Urea-chelated CRP (5 ml at 500 micrograms/ml) is emulsified with an equal volume of complete Freund's adjuvant for multiple subcutaneous, unilateral, paraspinal injections. Four booster inoculations of identical concentration are given in incomplete Freund's on opposite sides of the spine at 2 week intervals. Serum is fractioned with 45% ammonium sulfate and sequentially passaged over human albumin and SAP-affinity columns. This partially purified antiserum if further purified by passage over an affinity column on which urea-chelated CRP was immobilized on cyanogen-bromide activated BioGel (Bio-Rad Laboratories, Richmond, Calfi.). Specific antibody is eluted using Tris buffered saline (pH 7.4) containing 2 M $MgCl_2$ (final pH 4.5) and is equilibrated in 10 mM PBS (pH 7.4) containing 1% BSA.

This antibody may be used to bind immunoglobulin or immune complexes which contain, or which have been supplemented to contain, modified-CRP expressing neo-CRP.

Example 12

Plasma from a patient with Multiple Sclerosis (FIG. 4) and plasma from a patient with Myastinia Gravis (FIG. 5) were passed over columns containing cyanogen-bromide activated agarose resin to which modified-CRP (prepared as described Example 1) had been attached. After washing, with buffered saline (pH7.4) bound protein was eluted with buffered saline (pH 7.4) containing 1M $CaCl_2$.

Figure 4:
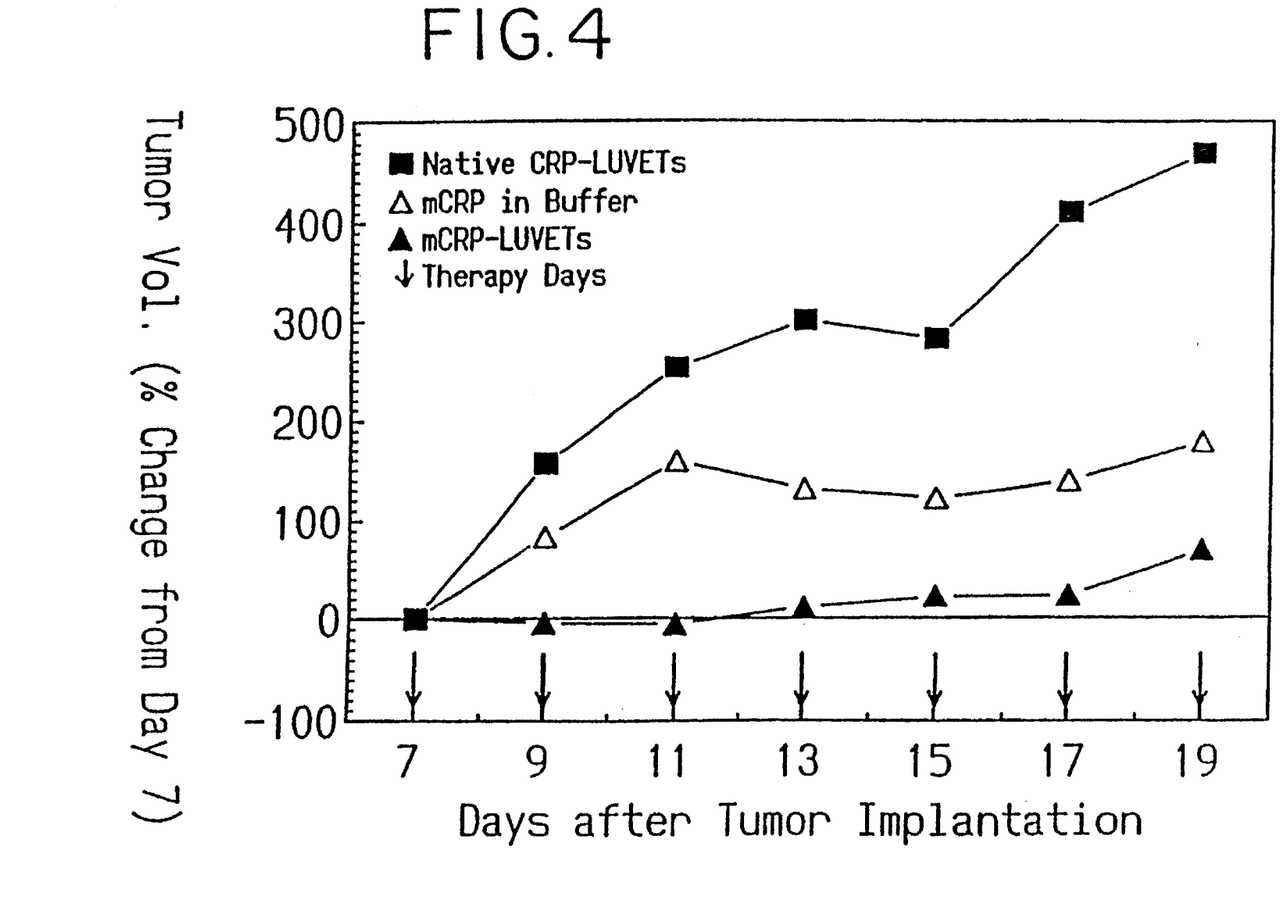
FIG. 4 shows the binding of immunoglobulin from the plasma of a patient having Multiple Sclerosis to unsubstituted agarose resin and to cyanogen bromide activated agarose resin to which modified-CRP has been attached.
Figure 5:
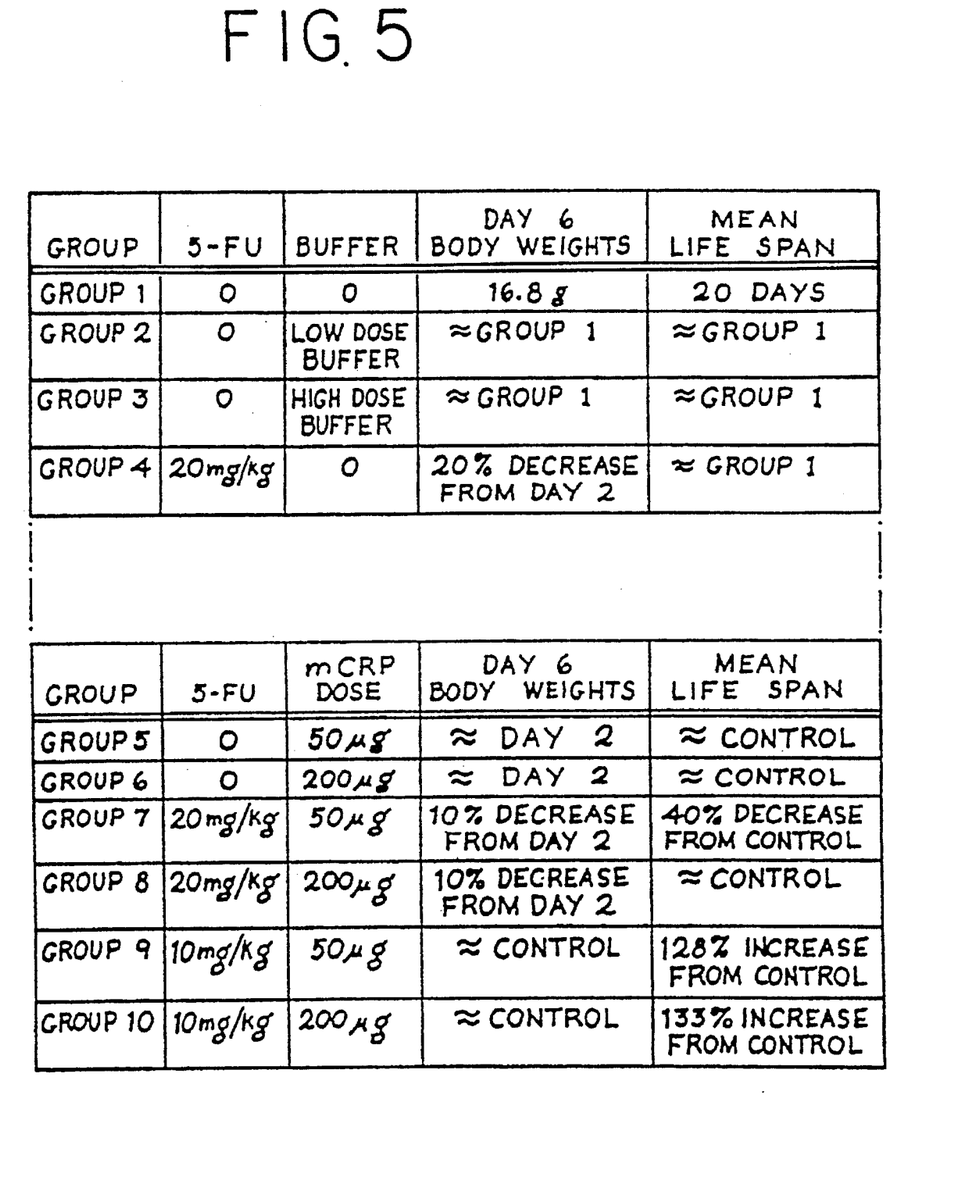
FIG. 5 shows the binding of immunoglobulin from the plasma of a patient having Myasthenia Gravis and from freeze-thawed normal plasma.

A large amount of protein was bound and eluted. When analyzed for content, the bound protein from both patient samples was found to be predominantly IgG (at least 90%). The majority of the protein from normal plasma was also identified as IgG.

The amount of protein bound to unsubstituted agarose from an identical aliquot of Multiple Sclerosis plasma is shown in FIG. 4. Also, the amount of protein bound to modified-CRP-agarose resin from freeze-thawed normal plasma is shown for comparison in FIG. 5. Freeze-thaw treatment of normal plasma is known to nonspecifically increase the level of aggregated IgG in the plasma sample. Thus, even though this test sample was "normal", a substantial amount of protein (IgG) bound to modified-CRP-agarose. Nonetheless, the amount of IgG from freeze-thawed normal plasma which did bind and elute from the column was only 25% to 40% of the amount of IgG that was bound from equal volumes of patient plasma.

Comparable results were obtained using modified-CRP prepared by direct immobilization on the agarose resin instead of modified-CRP prepared by urea-chelation.

Example 13

In vitro manipulation of CRP other than by urea-chelation to assess the effects of various treatments on the expression of neo-CRP antigenicity Aliquots of isolated CRP at 1 mg/ml were treated as follows: (1) CRP was heated at 63° C. in buffered saline for 2 minutes selectively in the presence of a chelating agent such as EDTA; (2) CRP in buffered saline was adjusted to pH 2.0 with HCl and incubated at ambient temperatures for 1 min prior to neutralization with NaOH; and (3) CRP was incubated with polystyrene beads or on other latex surfaces. CRP was also synthesized in vitro by molecular biology techniques. Using the antibody produced in Example 11 in a conventional immunoassay, it was determined that all of these procedures caused the expression of neo-CRP.

The preceding examples can be repeated with similar success by substituting the generically or specifically described reactants and/or operating conditions of this invention for those specifically used in the examples. From the foregoing descriptions, one skilled in the art to which this invention pertains can easily ascertain the essential characteristics thereof and, without departing from the spirit and scope of the present invention, can make various changes and modifications to adapt it to various usages and conditions.

What is claimed is:

1. A method of binding aggregated immunoglobulin or immune complexes comprising contacting the aggregated immunoglobulin or immune complexes with modified C-reactive protein which expresses neo-CRP antigenicity.

2. A method of removing aggregated immunoglobulin or immune complexes from a fluid comprising:
   contacting the fluid with modified C-reactive protein which expresses neo-CRP antigenicity so that the aggregated immunoglobulin or immune complexes bind to the modified C-reactive protein; and
   separating the fluid from the aggregated immunoglobulin or immune complexes bound to the modified C-reactive protein.

3. The method of claim 2 wherein the fluid is a body fluid taken from a mammal in need of removal of immune complexes.

4. The method of claim 3 wherein the body fluid is returned to the mammal after the immune complexes are removed.

5. A method of detecting or quantitating immune complexes comprising:

contacting the immune complexes with modified C-reactive protein which expresses neo-CRP antigenicity so that the immune complexes bind to the modified C-reactive protein; and detecting or quantitating the immune complexes bound to the modified C-reactive protein.

6. The method of claim 5 wherein the modified C-reactive protein is labeled prior to being contacted with the immune complexes to allow for the detection or quantitation of the immune complexes.

7. The method of claim 5 wherein a labeled component that binds to the immune complexes or to the modified C-reactive protein is added to allow the immune complexes to be detected or quantitated.

8. The method of claim 1, 2, 3, 4, 5 or 7 wherein the modified C-reactive protein is immobilized on a solid surface.

9. The method of claim 8 wherein the solid surface is hydrophobic.

10. The method of claim 8 wherein the solid surface is hydrophilic.

11. The method of claim 8 wherein the binding of C-reactive protein to the solid surface causes the expression of the neo-CRP antigenicity.

12. The method of claim 8 wherein a linking agent is employed to enhance the binding of the modified C-reactive protein to the solid surface.

13. A method of binding aggregated immunoglobulins or immune complexes comprising:

contacting the aggregated immunoglobulin or immune complexes with modified C-reactive protein that expresses neo-CRP; and simultaneously or later contacting the aggregated immunoglobulin or immune complexes with antibody to neo-CRP.

14. The method of claim 13 wherein the aggregated immunoglobulin or immune complexes are contained in a fluid, and the fluid is separated from the aggregated immunoglobulin or immune complexes bound to the antibody to neo-CRP thereby allowing for removal of the aggregated immunoglobulin or immune complexes from the fluid.

15. A device for removing aggregated immunoglobulin or immune complexes from fluids comprising:

modified C-reactive protein bound to a solid surface; and a means for encasing the solid surface so that the fluid may be contacted with the solid surface.

16. A package containing at least one container, the container holding modified C-reactive protein which expresses neo-CRP antigenicity.

17. The package of claim 16 wherein the materials in the package further include a container holding a labeled component which binds to immune complexes or modified C-reactive protein.

18. The package of claim 16 wherein the modified C-reactive protein is labeled.

19. A package containing materials useful for detecting or quantitating immune complexes, the materials in the package including at least a container holding modified C-reactive protein which expresses neo-CRP antigenicity and a container holding antibody which binds to modified C-reactive protein which expresses neo-CRP antigenicity.

\* \* \* \* \*